(12) United States Patent
Kondo

(10) Patent No.: US 6,529,754 B2
(45) Date of Patent: Mar. 4, 2003

(54) BIOMETRIC MEASURING DEVICE

(75) Inventor: Yutaka Kondo, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/403,240

(22) PCT Filed: Feb. 16, 1999

(86) PCT No.: PCT/JP99/00666

§ 371 (c)(1),
(2), (4) Date: Nov. 30, 1999

(87) PCT Pub. No.: WO99/40843

PCT Pub. Date: Aug. 19, 1999

(65) Prior Publication Data

US 2002/0151775 A1 Oct. 17, 2002

(30) Foreign Application Priority Data

Feb. 16, 1998 (JP) .......................... 10-033155
Sep. 4, 1998 (JP) .......................... 10-251337
Sep. 10, 1998 (JP) .......................... 10-257233

(51) Int. Cl.[7] .................................................. A61B 5/00
(52) U.S. Cl. ...................................... 600/344; 600/335
(58) Field of Search ......................... 600/309–311, 316, 600/322–324, 326, 334–335, 340, 344, 364–365, 502–503, 473–480; 224/170–178; 368/281–283, 286, 300

(56) References Cited

U.S. PATENT DOCUMENTS

| | | | | | |
|---|---|---|---|---|---|
| 1,275,769 A | * | 8/1918 | Scott | ........................... | 224/171 |
| 2,227,131 A | * | 12/1940 | Friedman | ..................... | 368/281 |
| 2,558,007 A | * | 6/1951 | Smith et al. | ................. | 224/175 |
| RE24,502 E | * | 7/1958 | Myerson | ..................... | 224/175 |
| 2,895,658 A | * | 7/1959 | Dzus | ........................... | 224/171 |
| 3,712,049 A | * | 1/1973 | Luxembourg | ............... | 368/281 |
| 4,185,621 A | * | 1/1980 | Morrow | ....................... | 600/485 |
| 4,280,506 A | * | 7/1981 | Zurcher | ...................... | 600/503 |
| 4,295,472 A | * | 10/1981 | Adams | ......................... | 600/503 |
| 4,865,038 A | * | 9/1989 | Rich et al. | ................... | 600/344 |
| 4,879,702 A | * | 11/1989 | Gardner | ...................... | 368/282 |
| 4,896,676 A | * | 1/1990 | Sasaki | ......................... | 600/494 |
| 5,504,474 A | * | 4/1996 | Libman et al. | ............. | 340/572 |
| 5,766,131 A | | 6/1998 | Kondo et al. | | |
| 5,807,267 A | * | 9/1998 | Bryars et al. | ............... | 600/500 |
| 5,823,409 A | * | 10/1998 | Kennedy | ...................... | 224/174 |
| 5,833,602 A | * | 11/1998 | Osemwota | .................. | 600/310 |
| 5,848,030 A | * | 12/1998 | Sullivan | ...................... | 368/282 |

FOREIGN PATENT DOCUMENTS

| | | |
|---|---|---|
| JP | 55-127513 | 9/1980 |
| JP | 61-72211 | 5/1986 |
| JP | 61-172518 | 10/1986 |
| JP | 62-159719 | 10/1987 |
| JP | 3-13807 | 2/1991 |
| JP | 5-88314 | 12/1993 |
| JP | 5-329117 | 12/1993 |
| JP | 8-84705 | 4/1996 |
| JP | 9-10183 | 1/1997 |
| JP | 9-108191 | 4/1997 |

* cited by examiner

*Primary Examiner*—Eric F. Winakur
*Assistant Examiner*—Matthew Kremer

(57) ABSTRACT

A watch-type biometric measuring device having a pulse wave sensor unit for detecting a pulse rate by a reflective optical sensor, a housing 10 storing therein the sensor unit, and a wristband 20 is improved. The wristband 20 has short band pieces 21 and 23 near the housing 10, and long band pieces 22 and 24 far from the housing 10. The band pieces 21 and 23 have high flexibility, and permit movement of a living body. On the other hand, the band pieces 22 and 24 have low flexibility, and secure holding ability against the living body. With this configuration, it is possible to mount the biometric measuring device on a measurement site of the living body with high adhesion while minimizing the sensation of pressure.

35 Claims, 29 Drawing Sheets

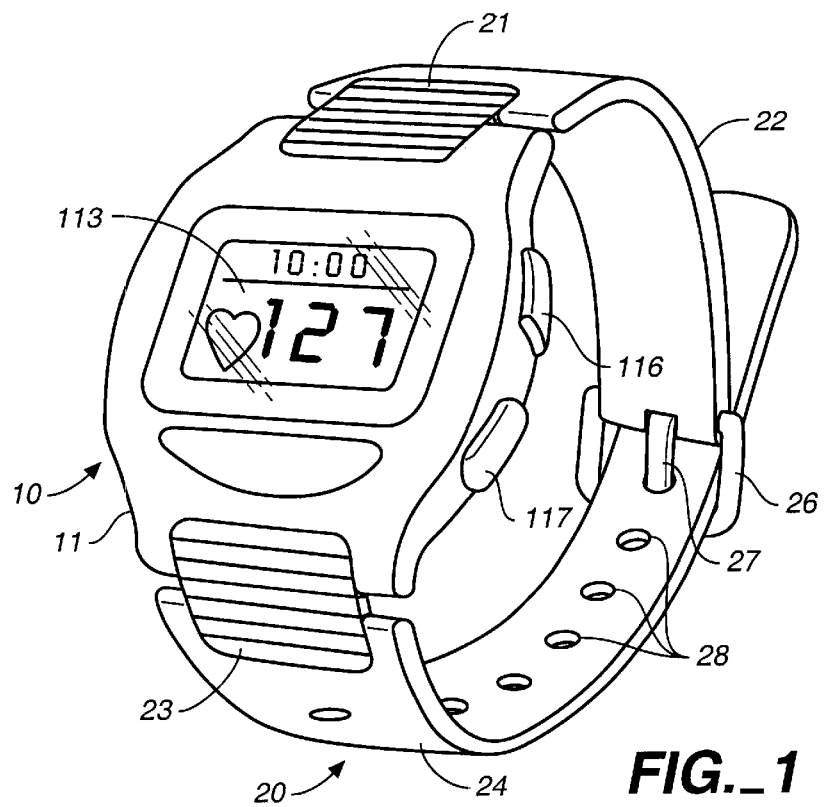
FIG._1
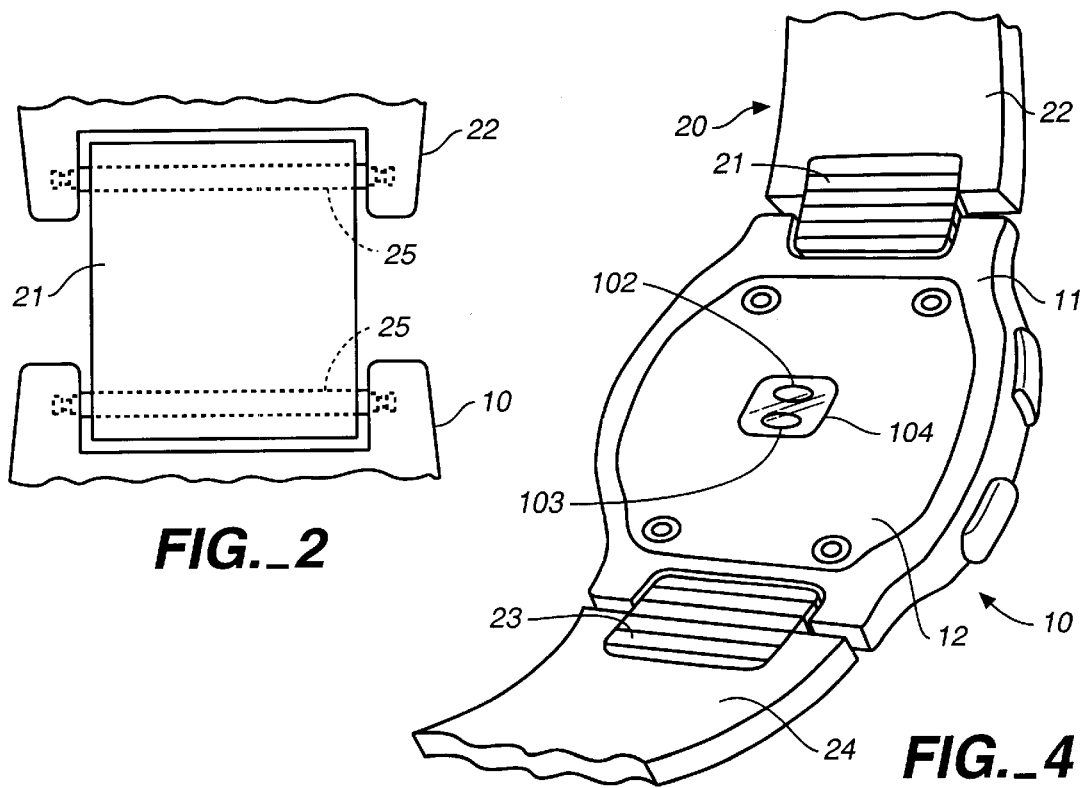
FIG._2
FIG._4

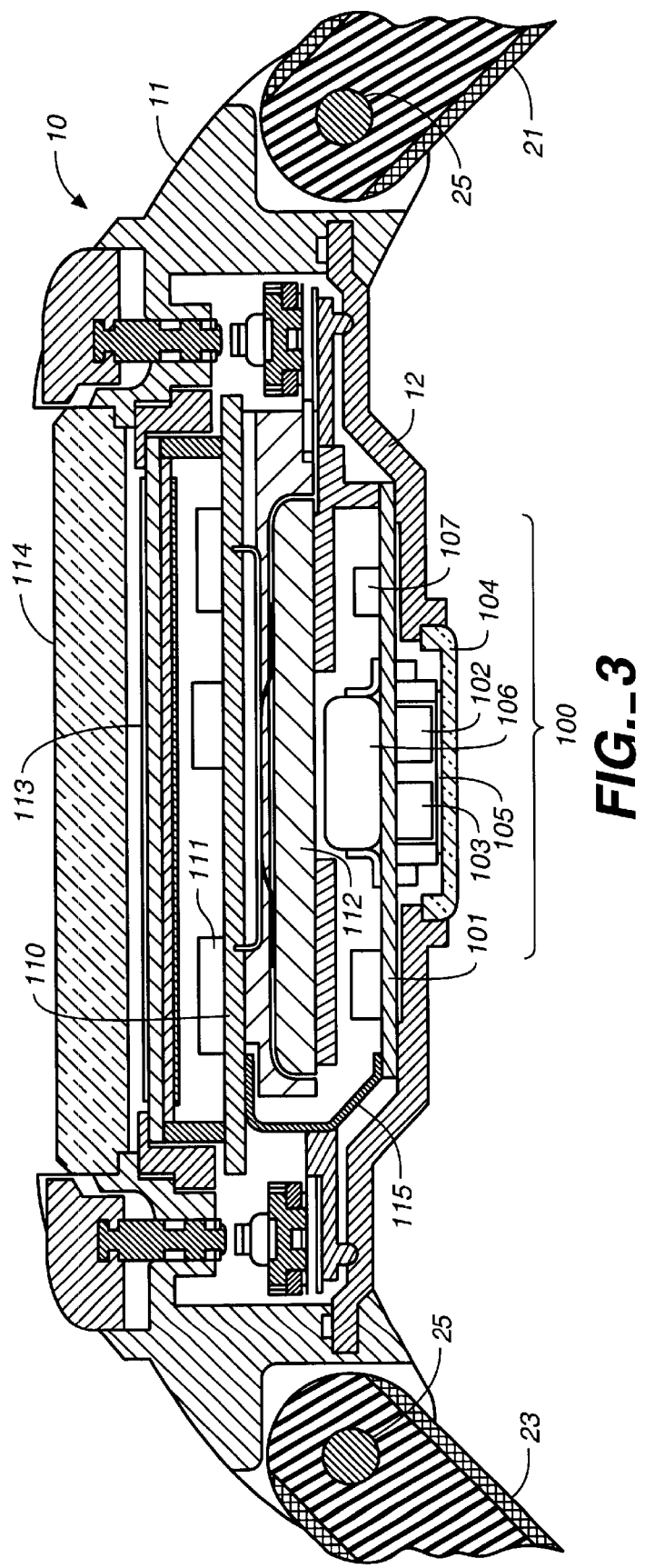
FIG._3

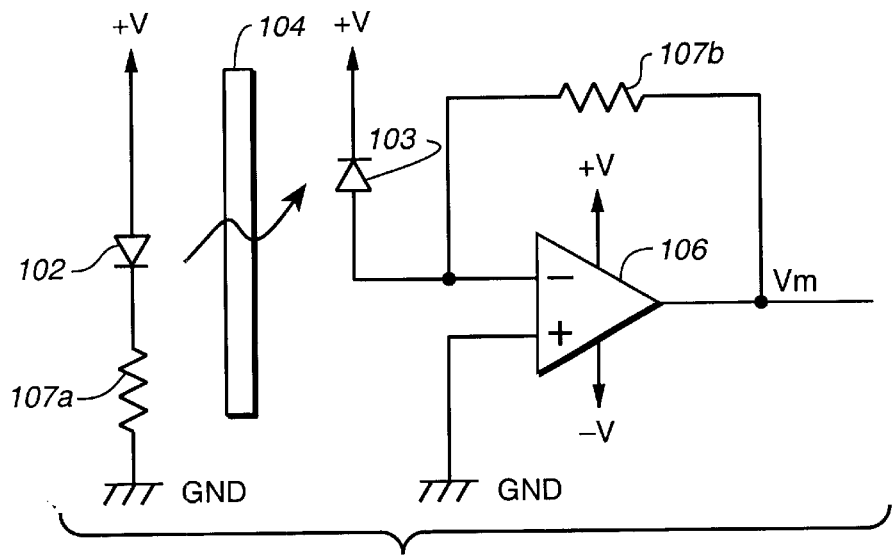
FIG._5
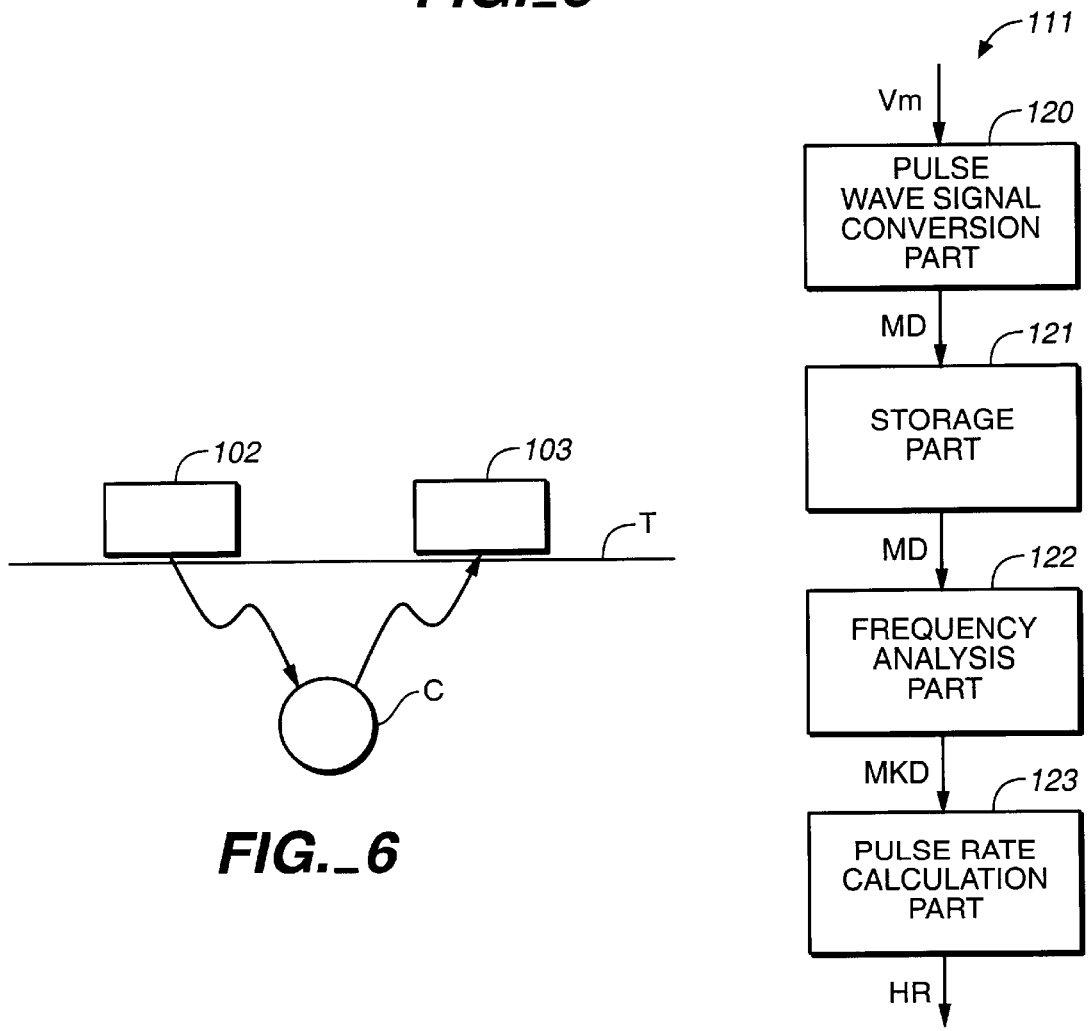
FIG._6
FIG._9

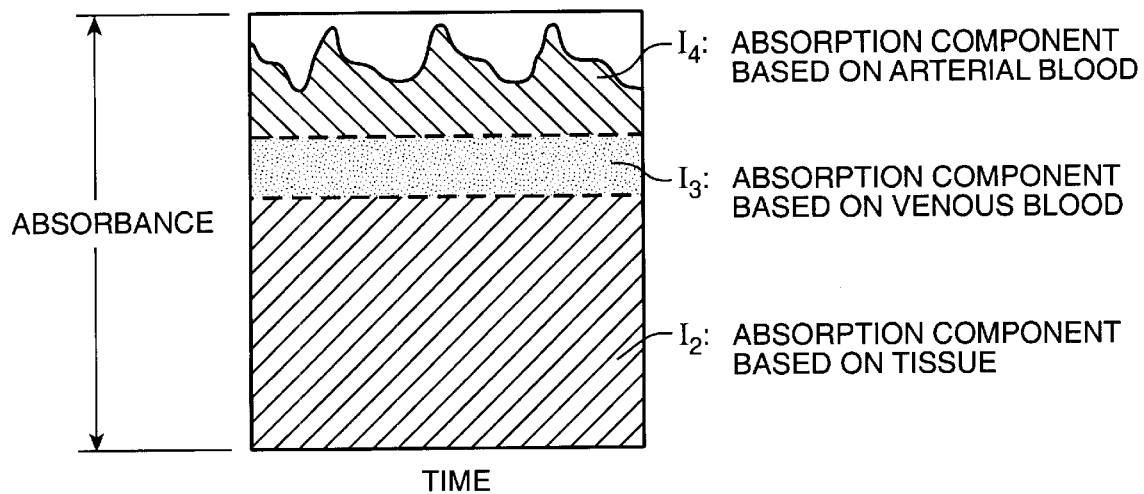
FIG._7
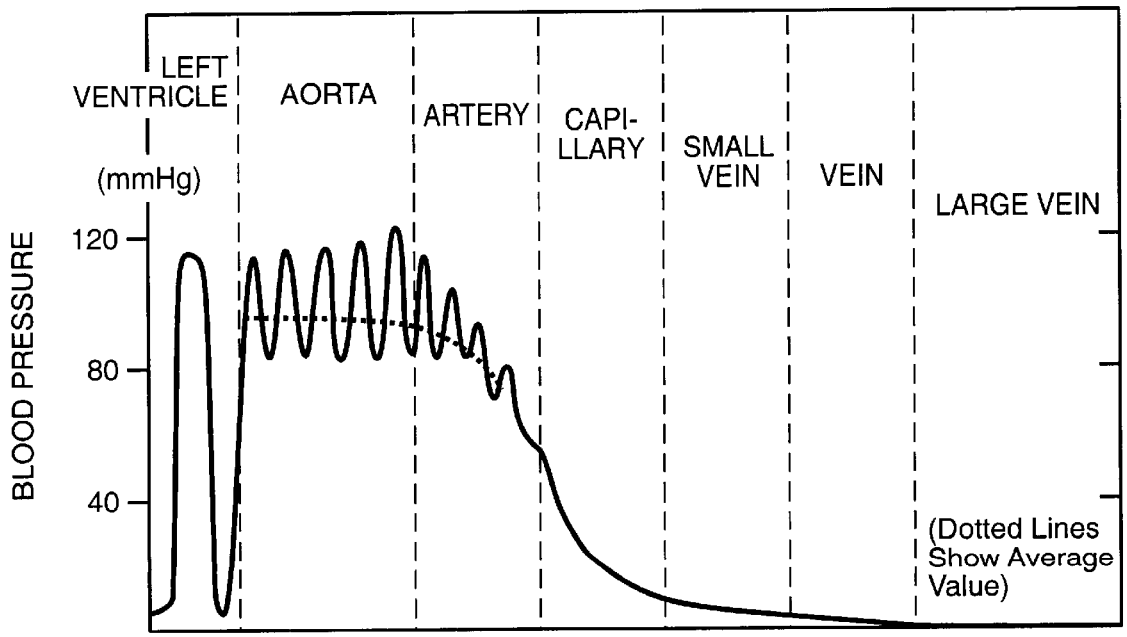
FIG._8

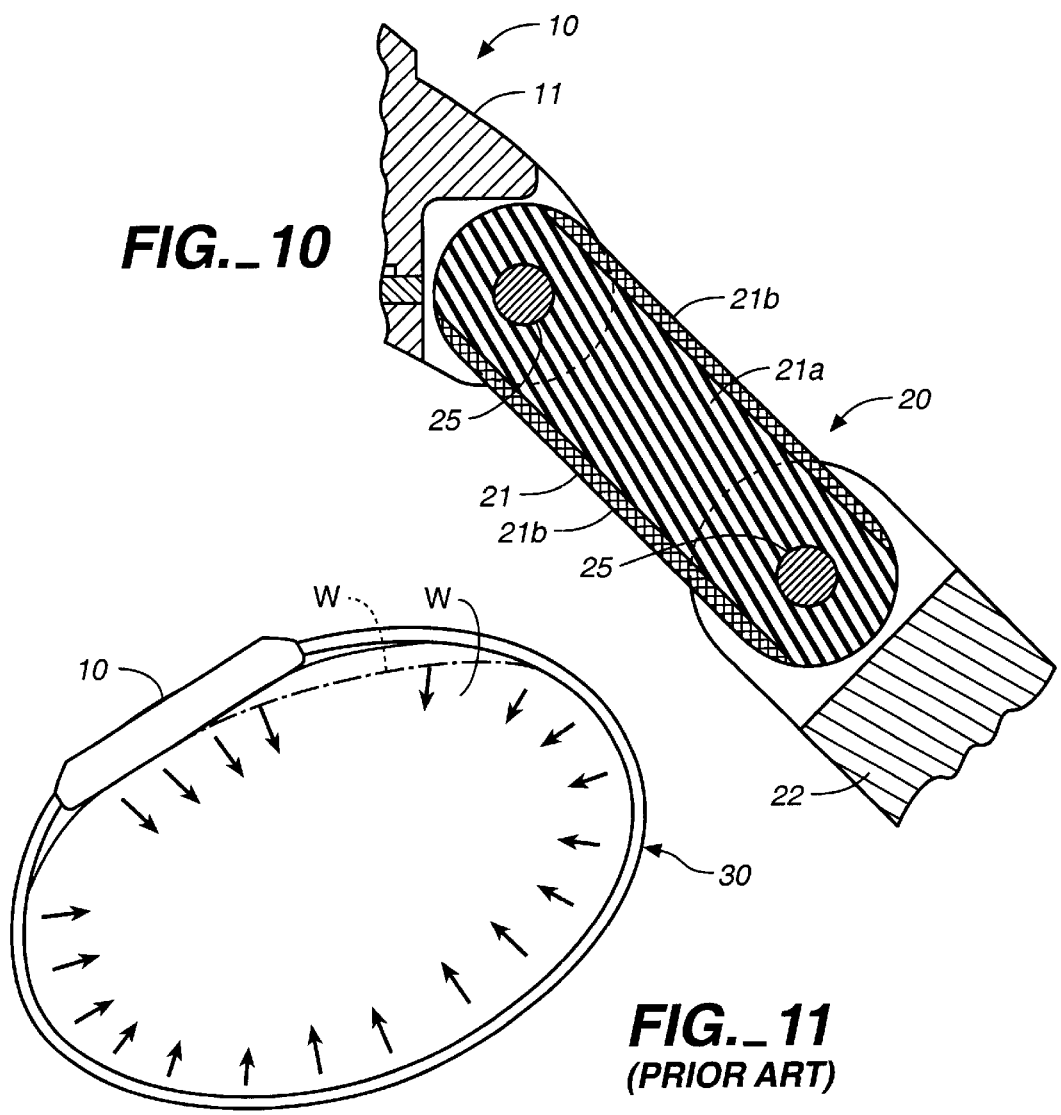
FIG._10
FIG._11
(PRIOR ART)
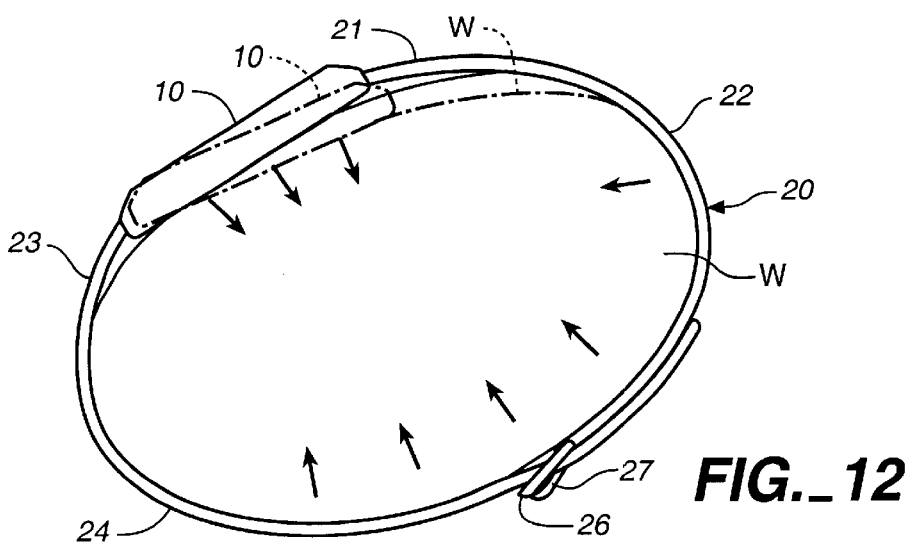
FIG._12

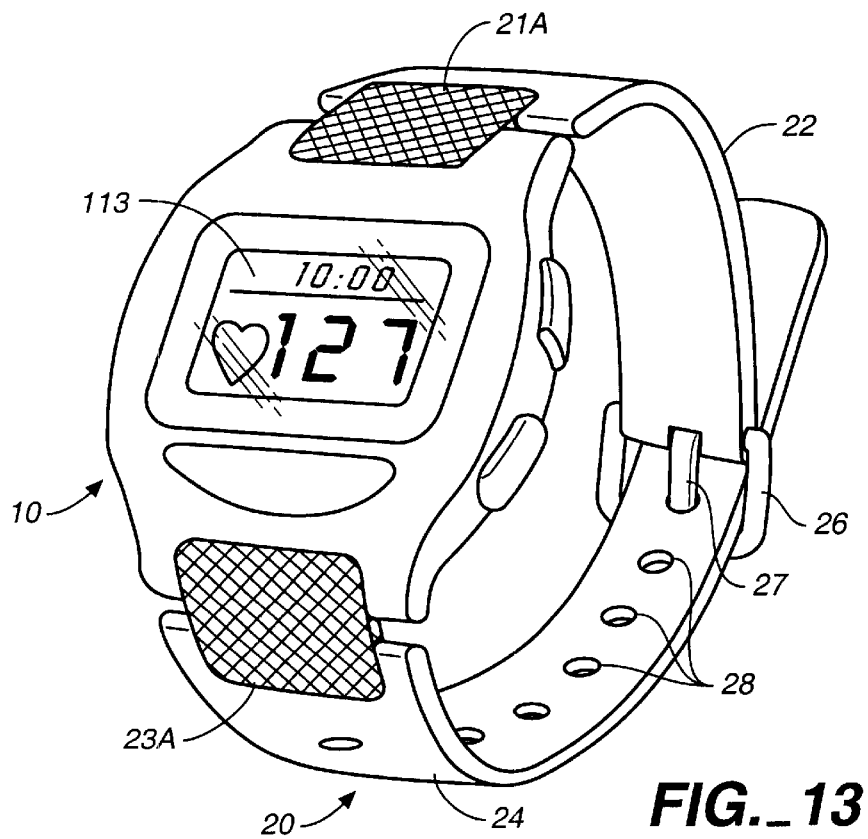
*FIG._13*
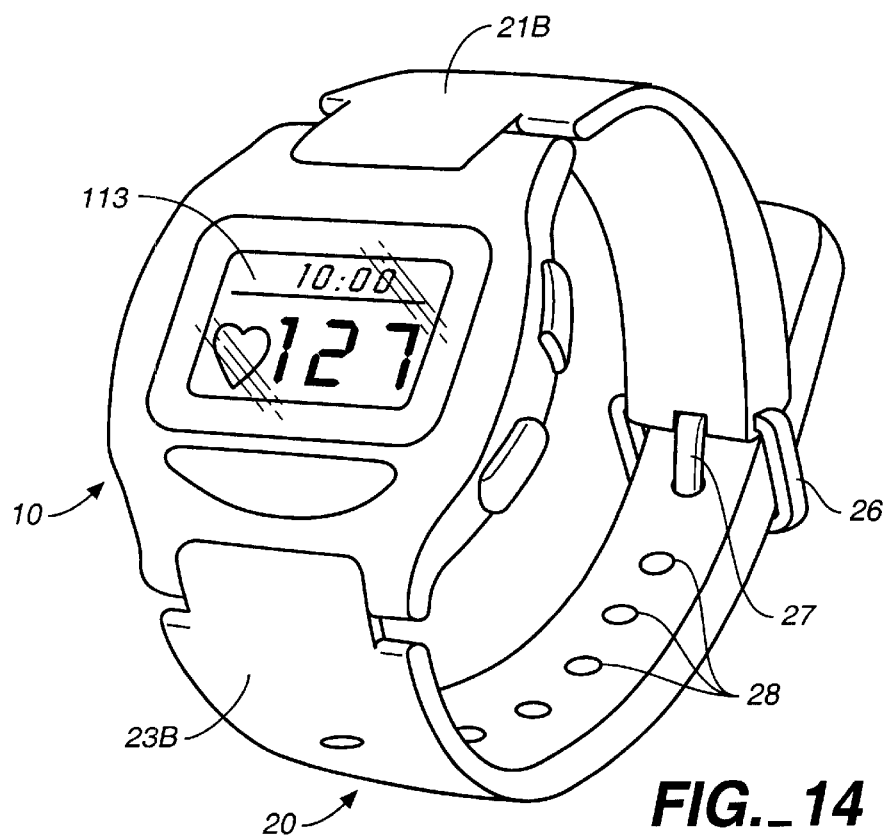
*FIG._14*

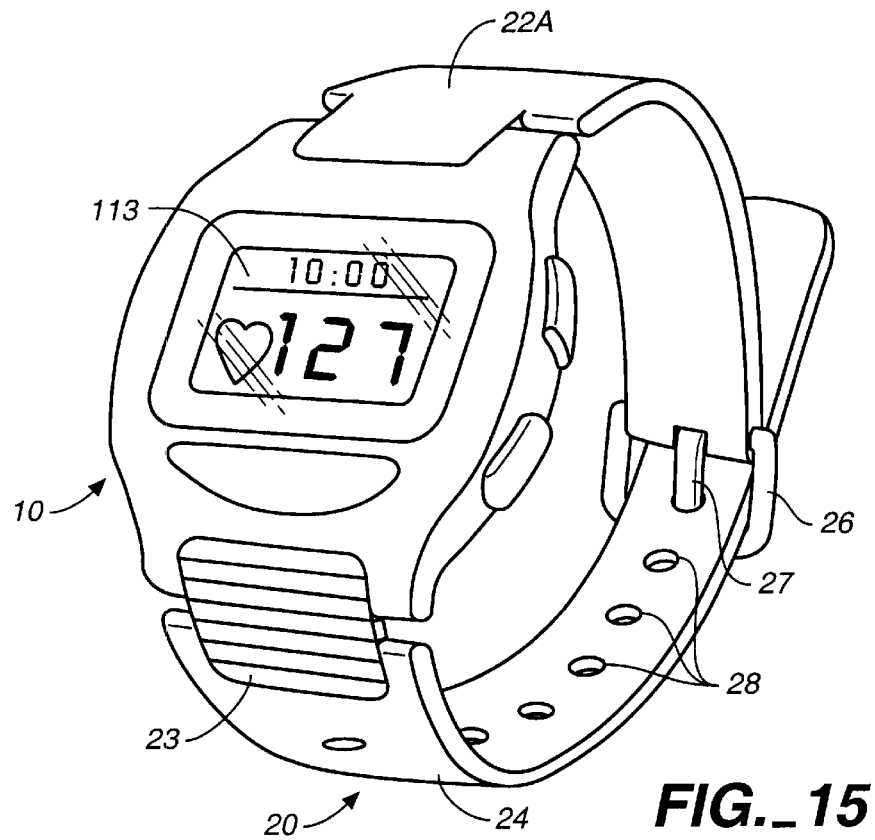
FIG._15
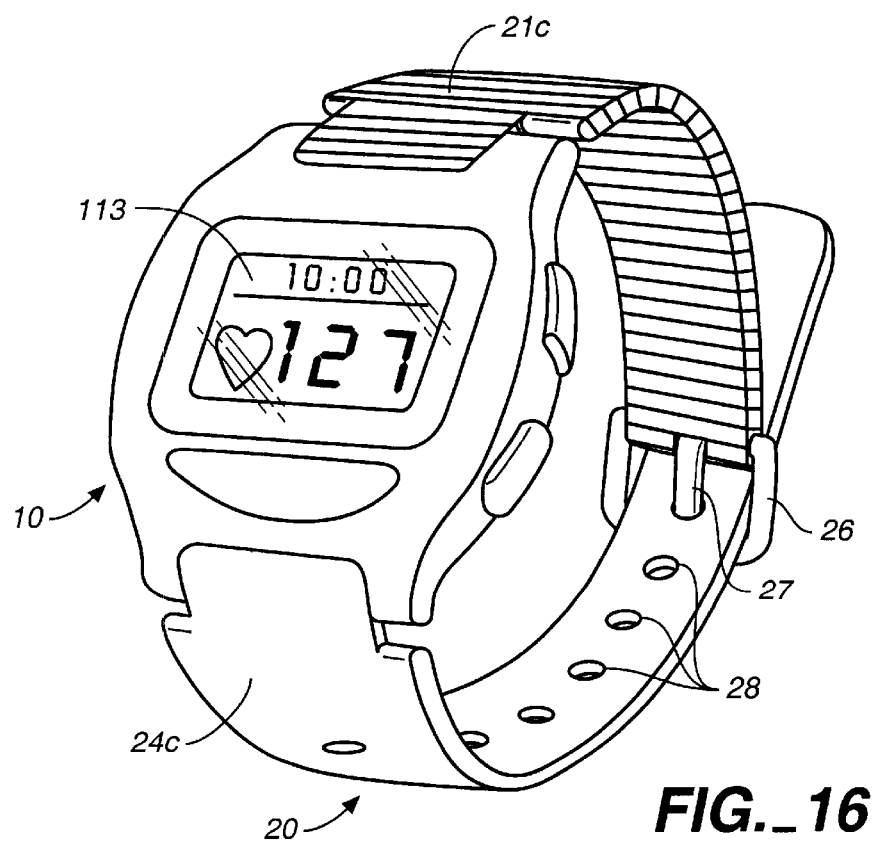
FIG._16

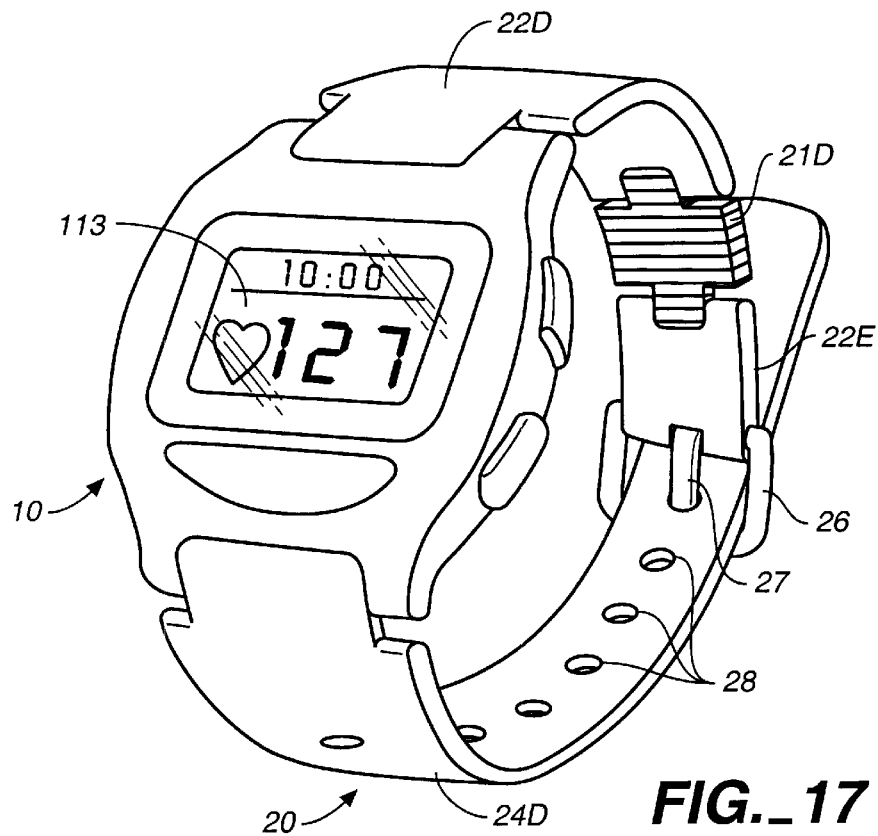
FIG._17
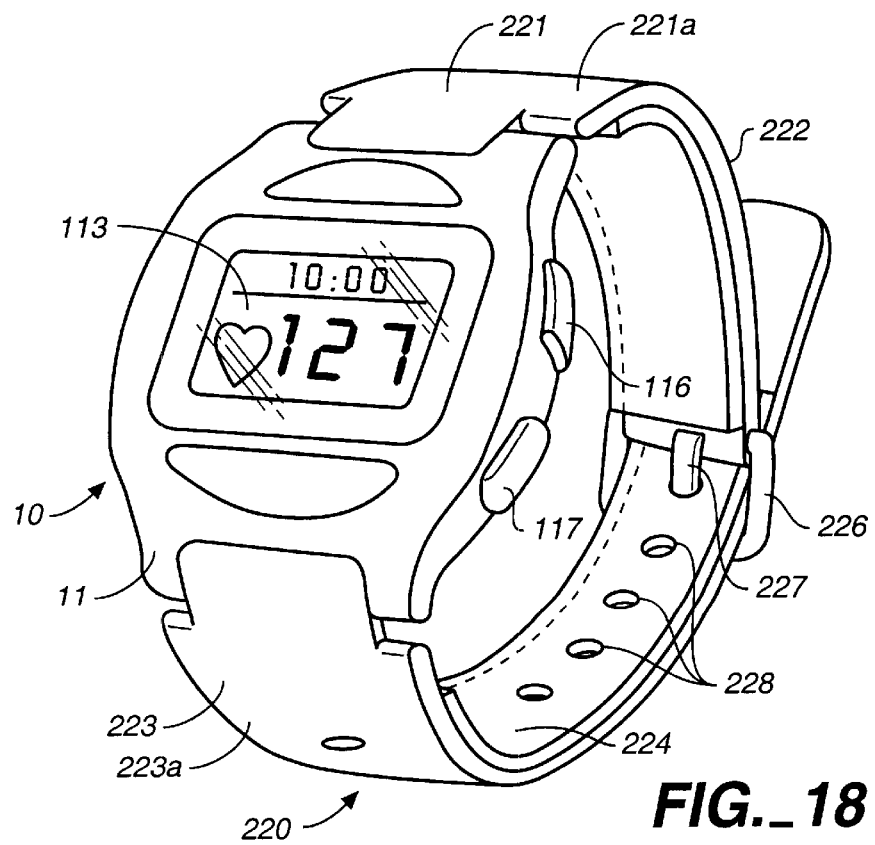
FIG._18

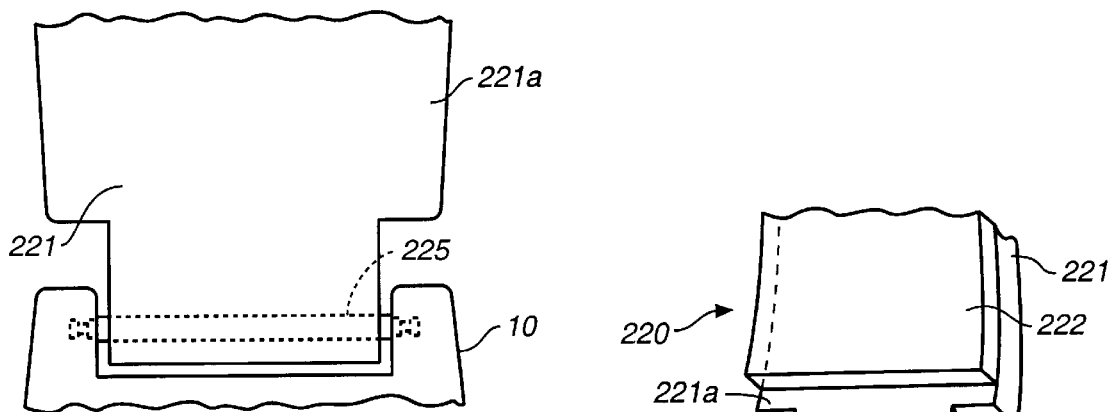
FIG._19
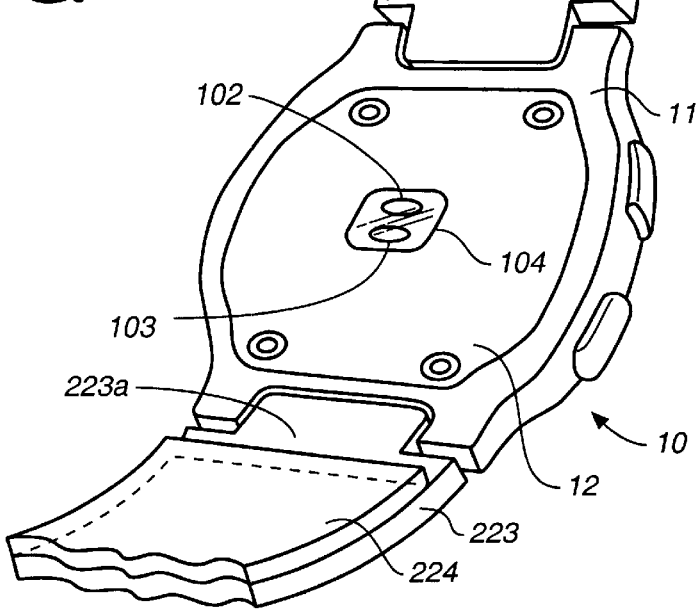
FIG._21
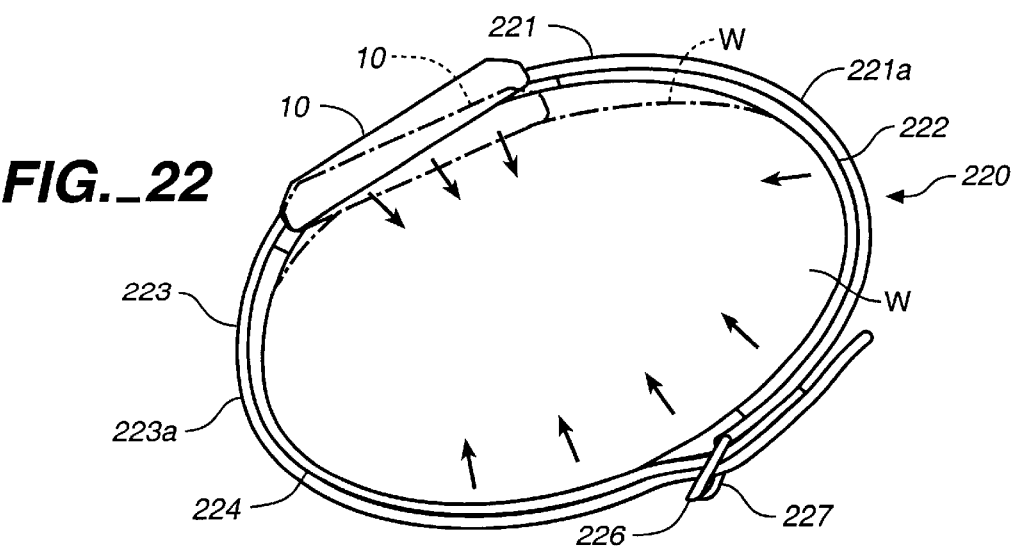
FIG._22

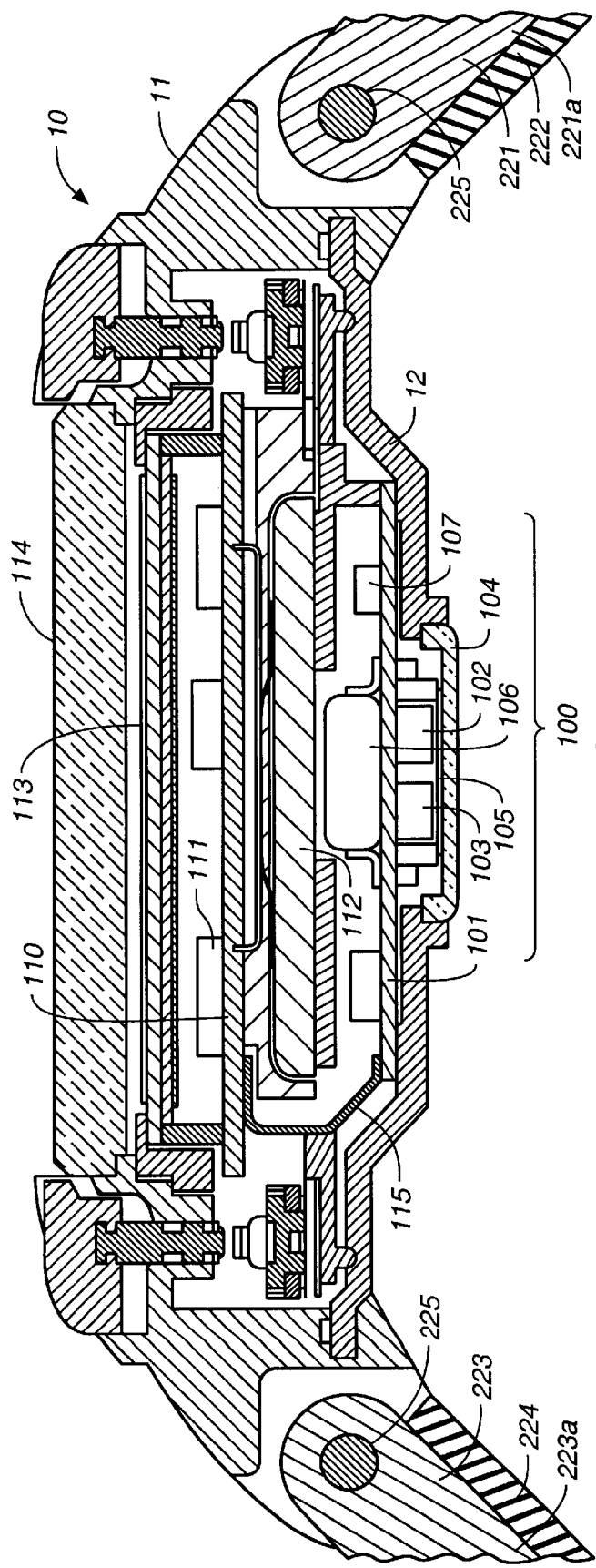
FIG._20

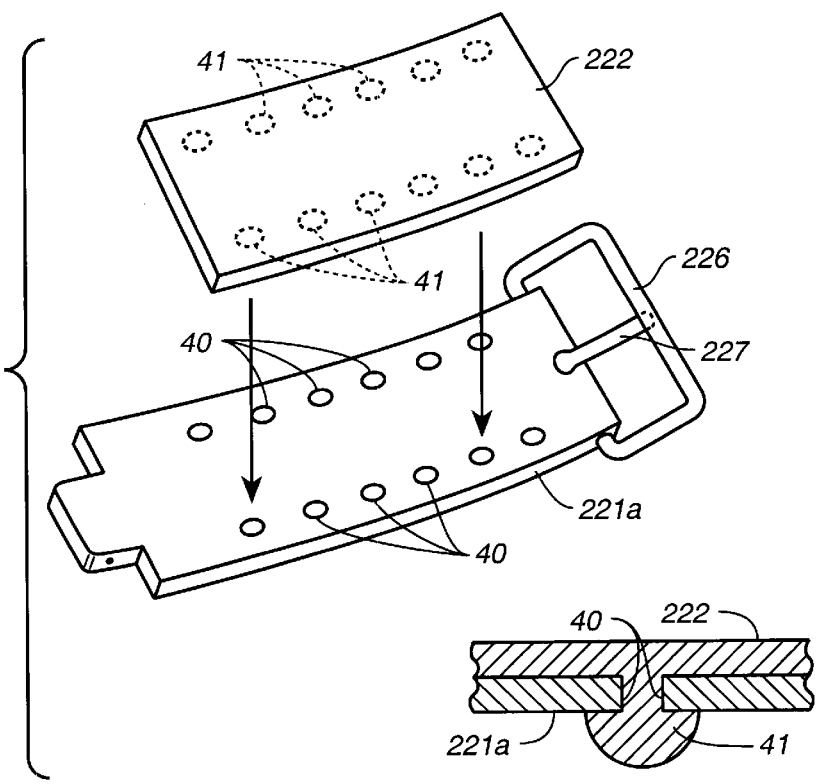
FIG._23
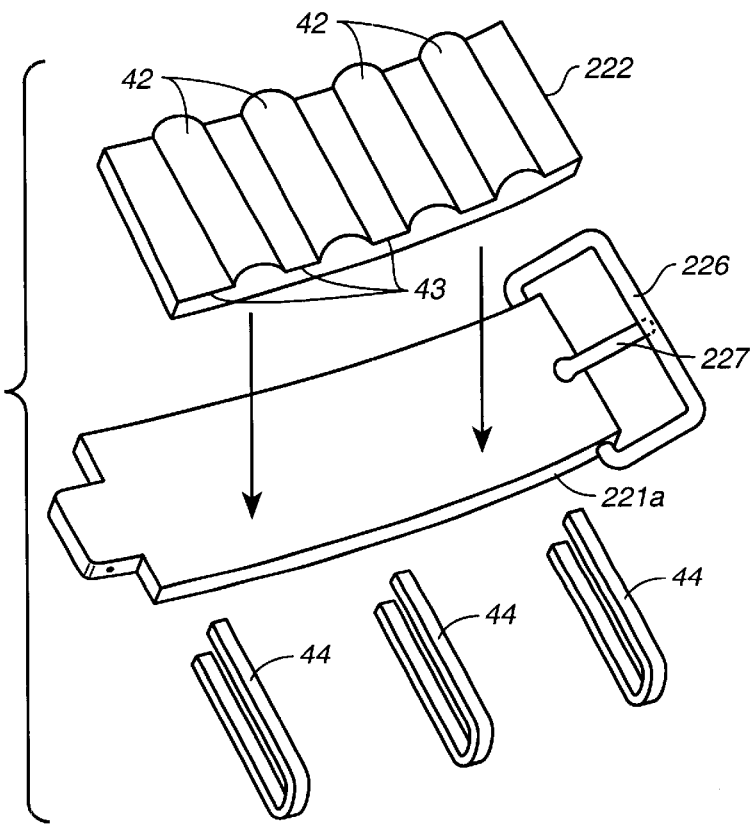
FIG._24

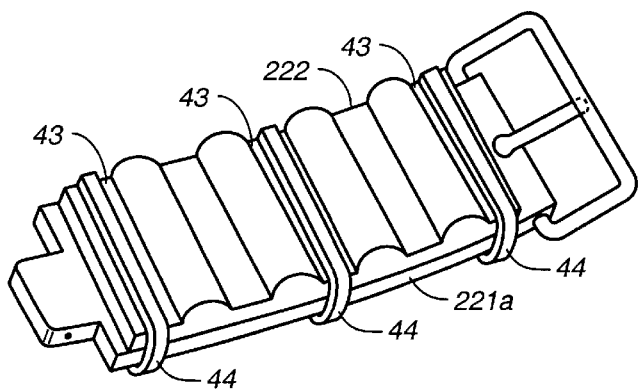
FIG._25
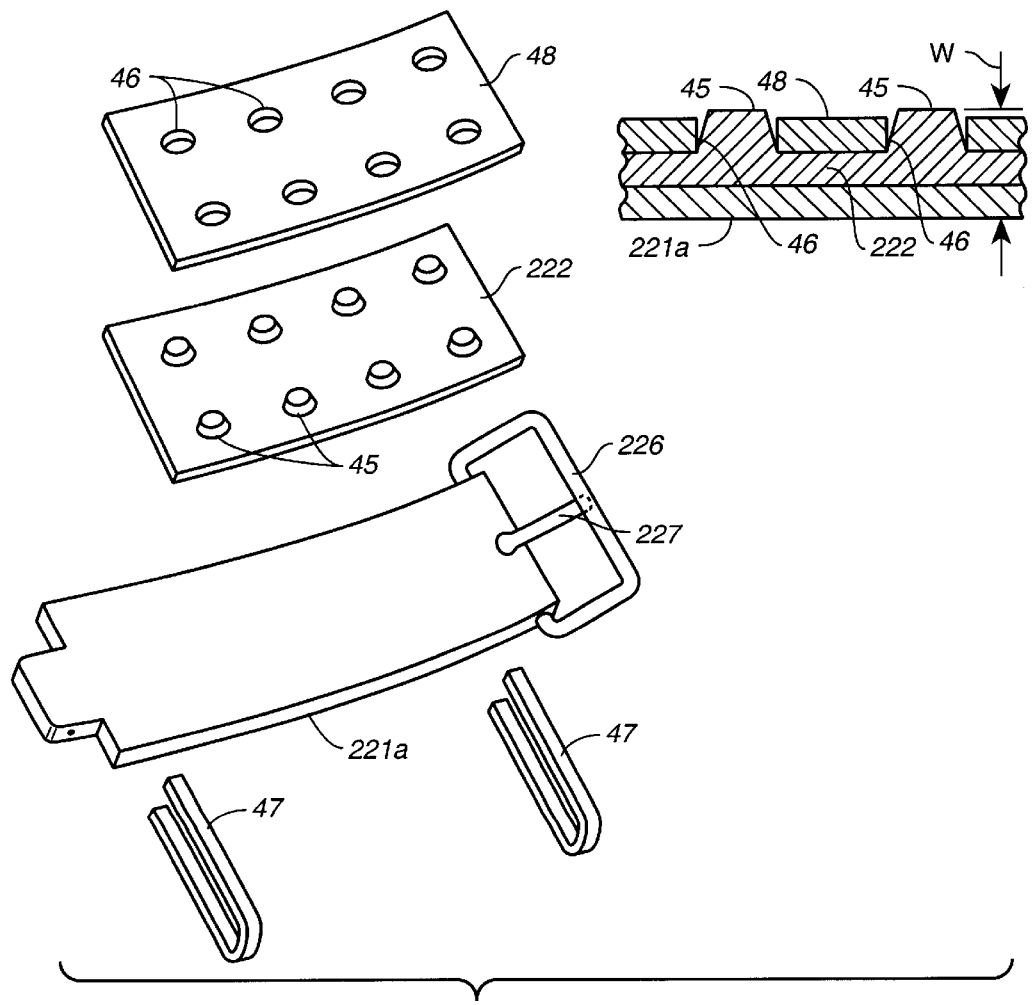
FIG._26

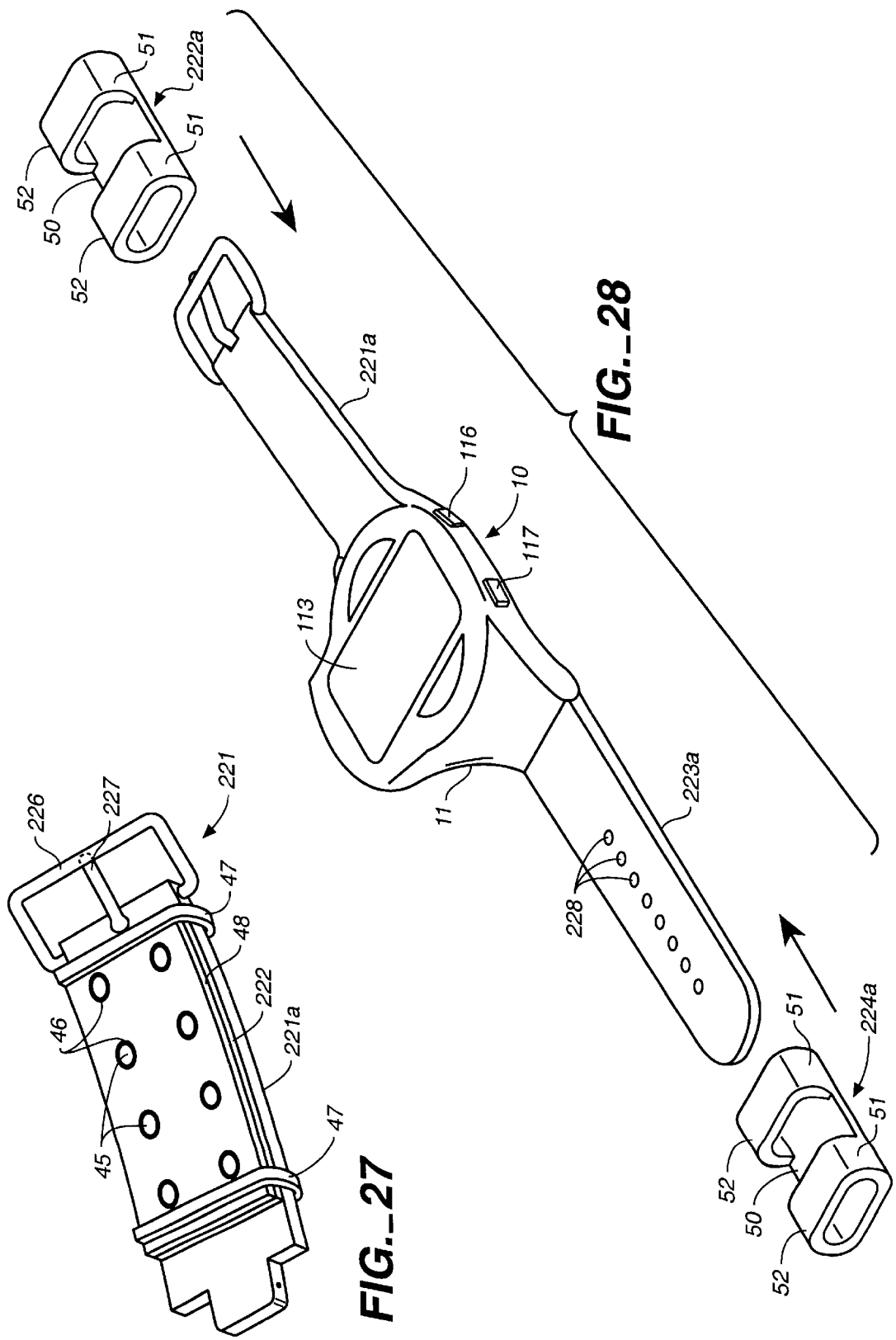

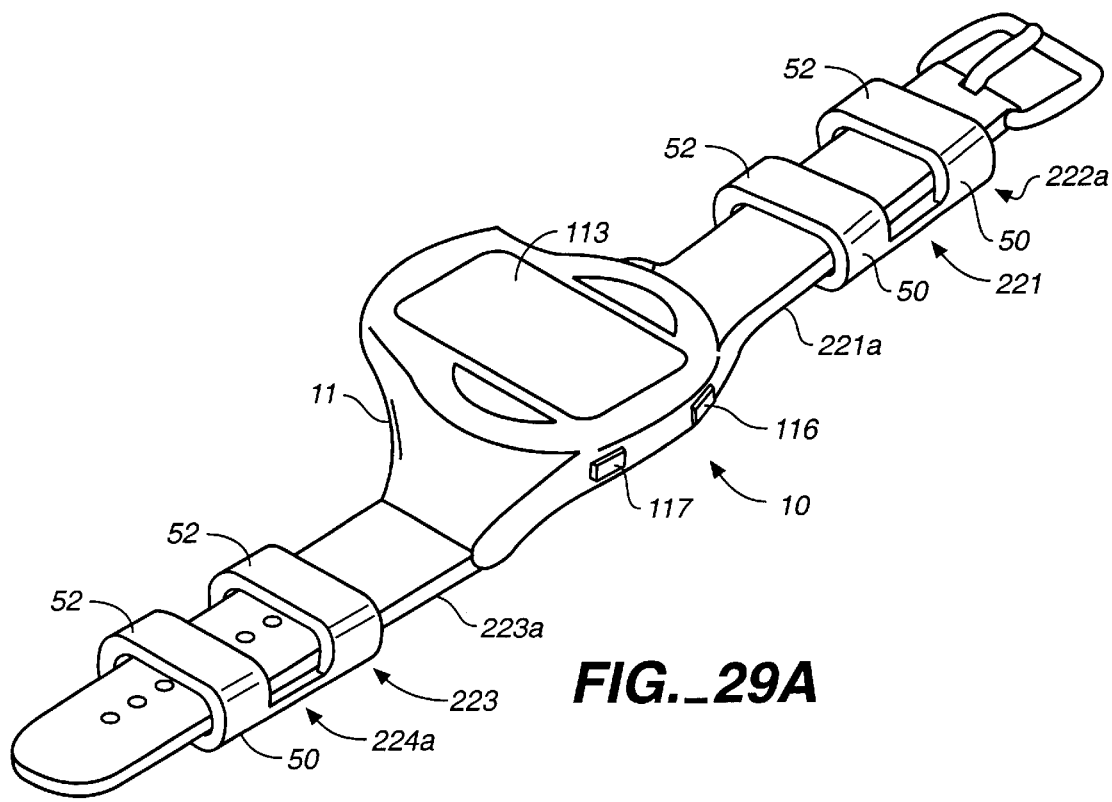
FIG._29A
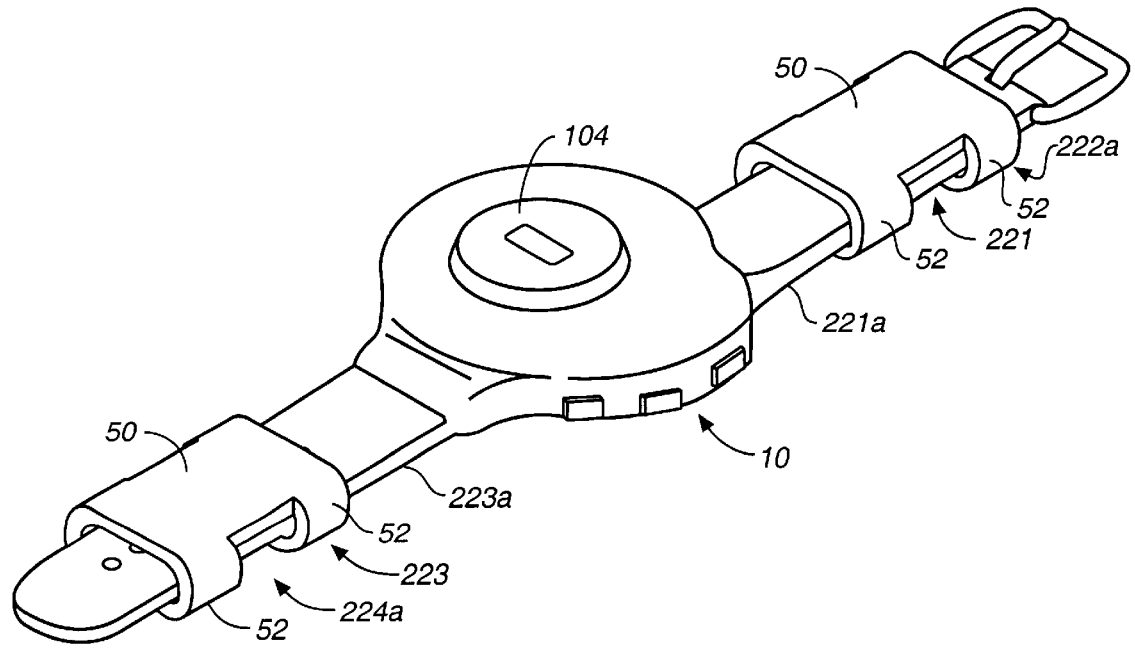
FIG._29B

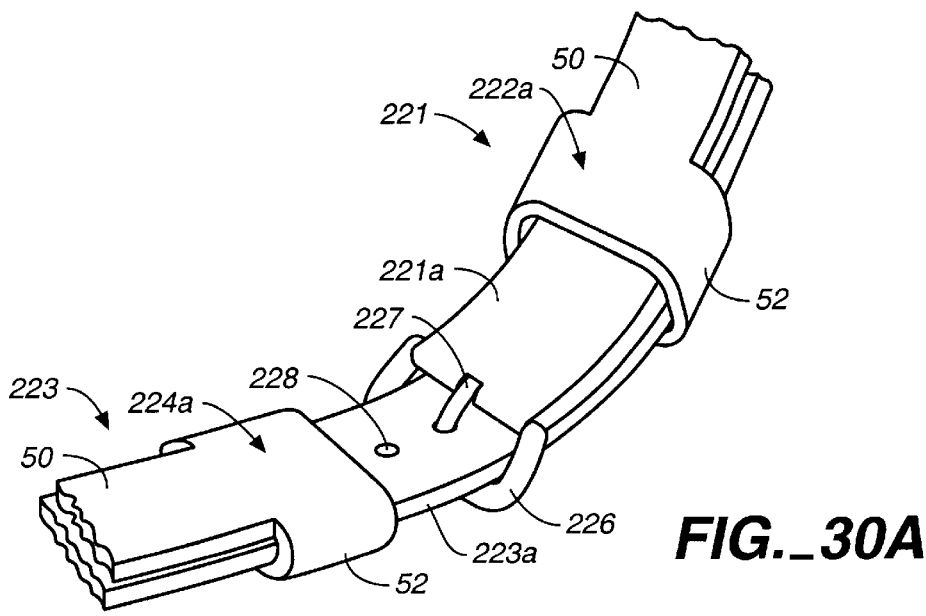
FIG._30A
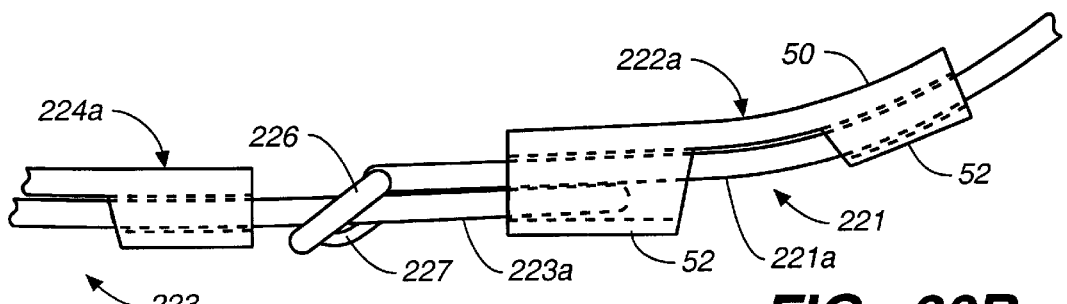
FIG._30B
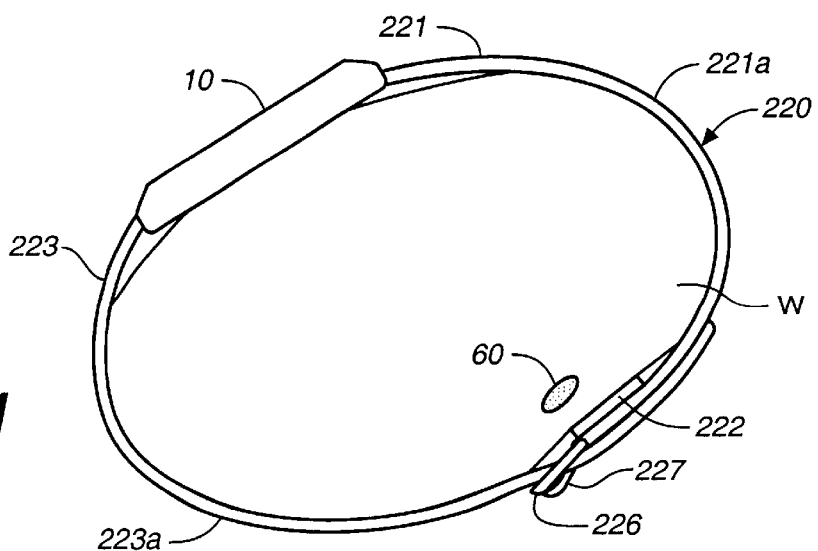
FIG._31

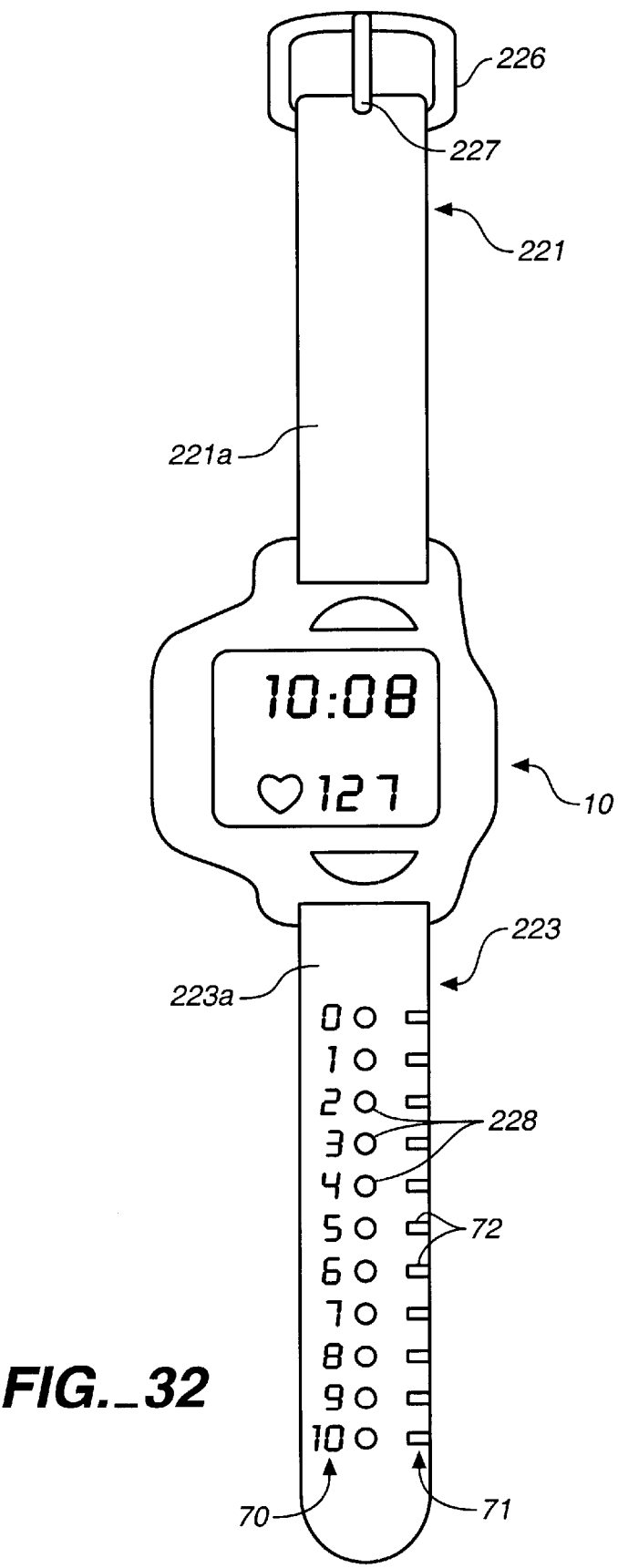
FIG._32

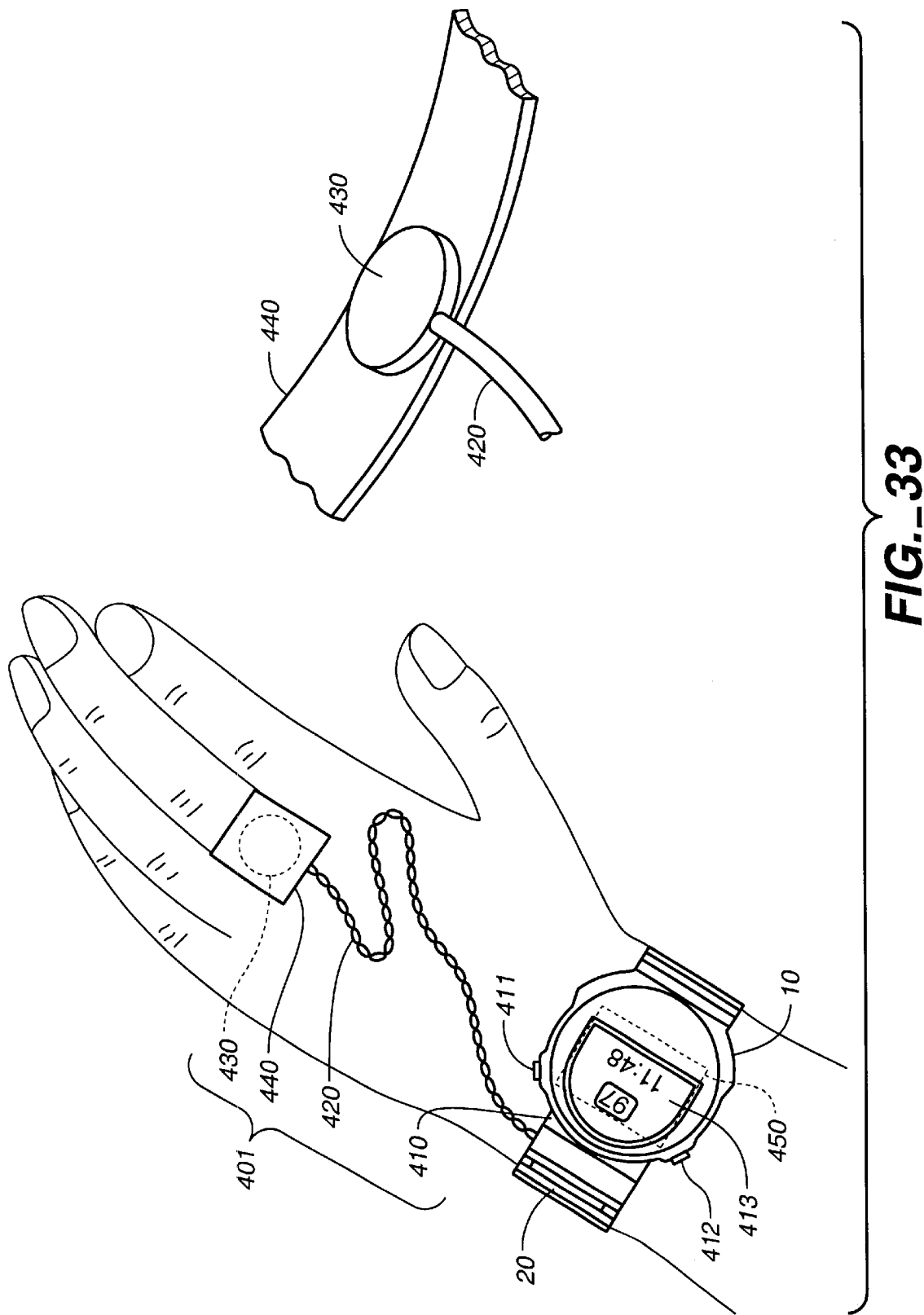
FIG._33

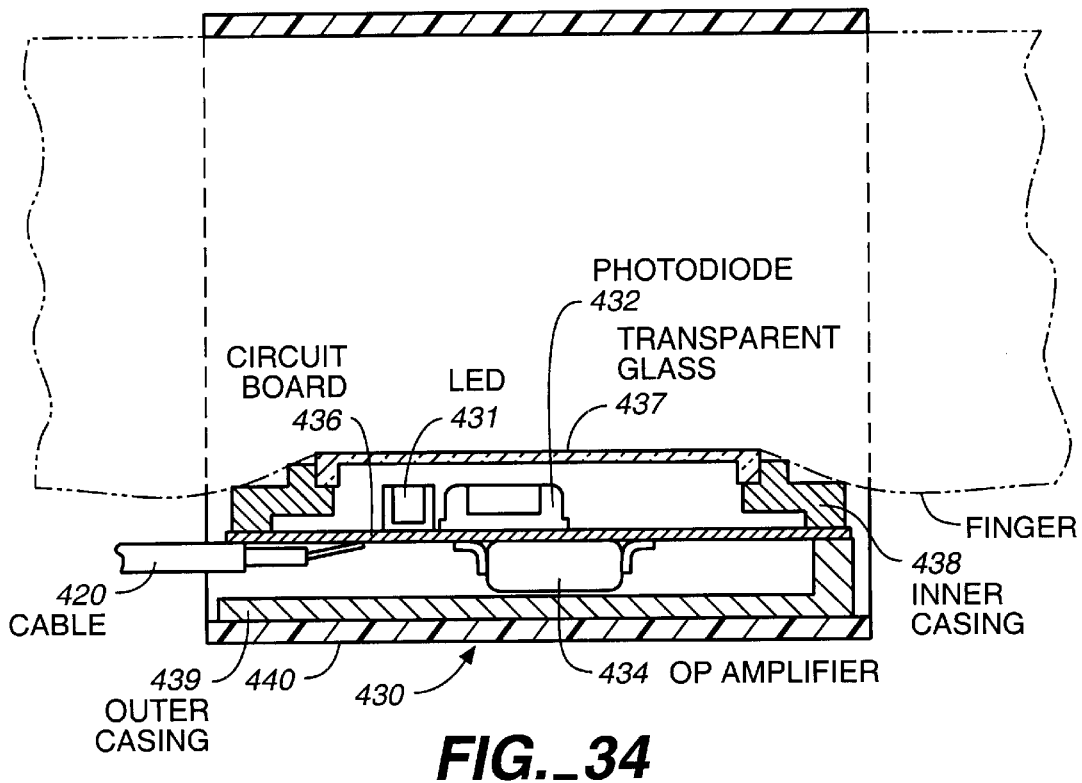
FIG._34
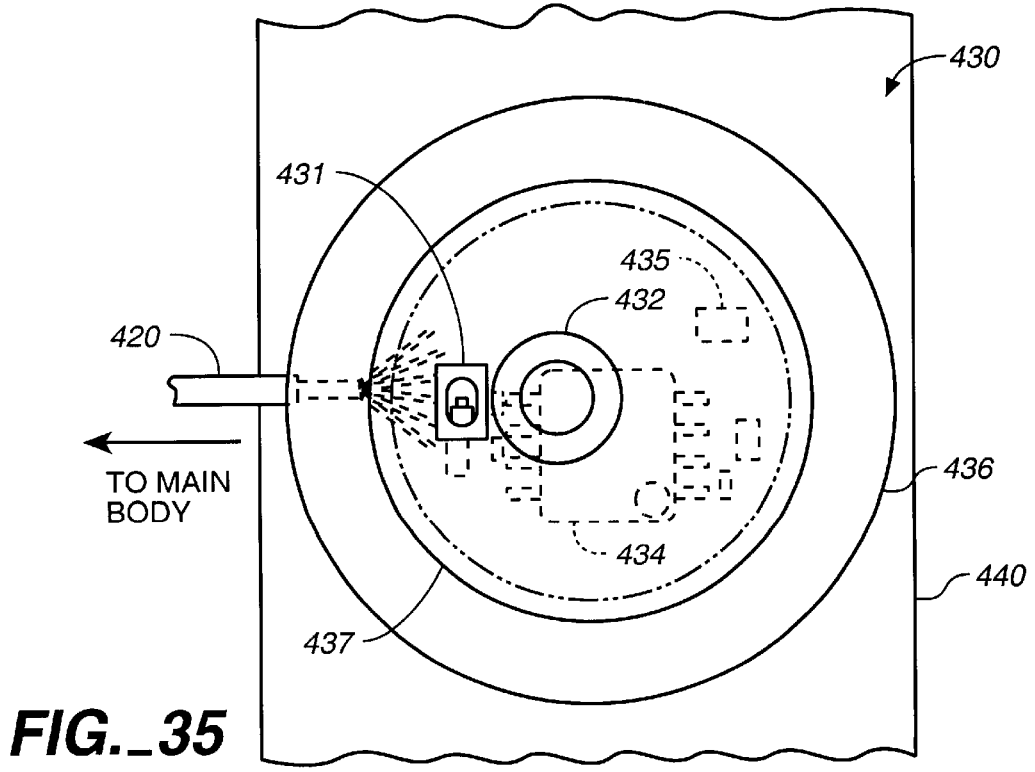
FIG._35

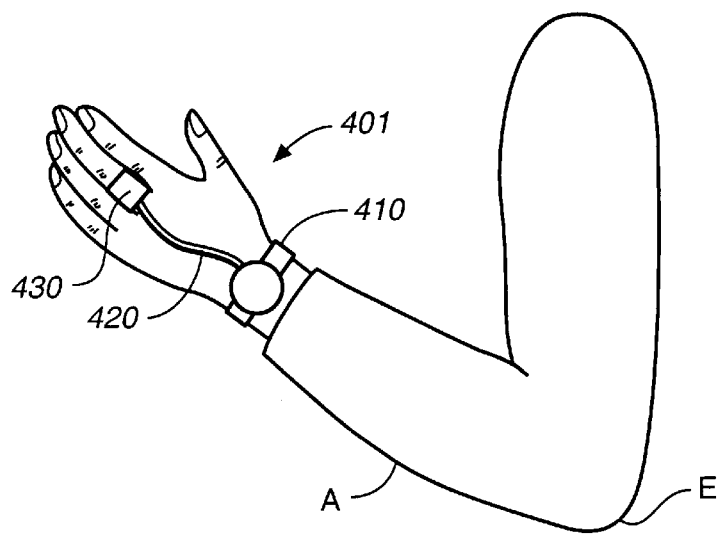
FIG._36A
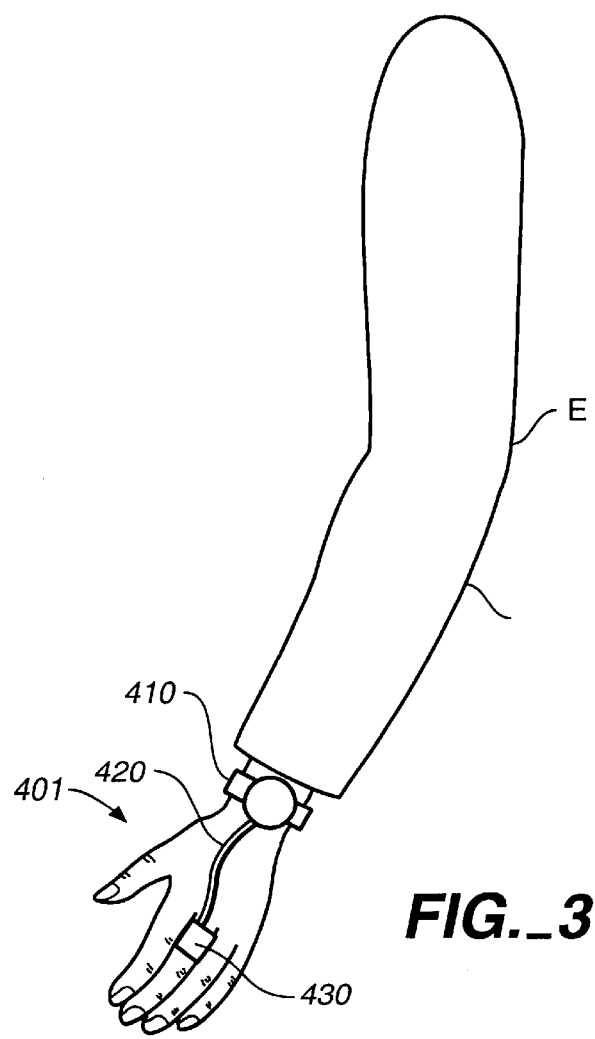
FIG._36B

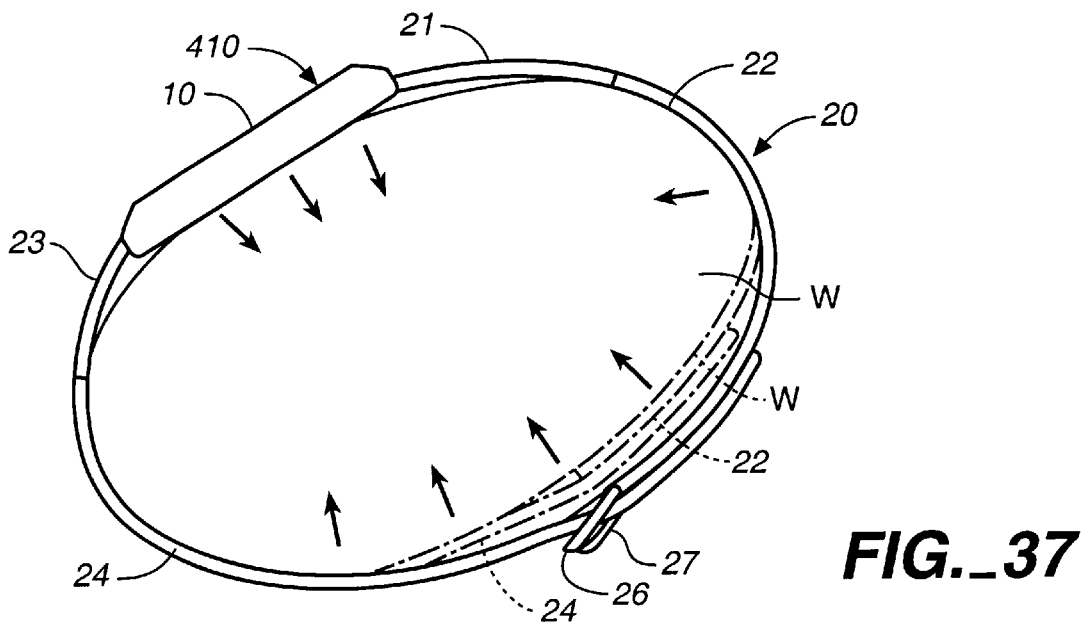
FIG._37
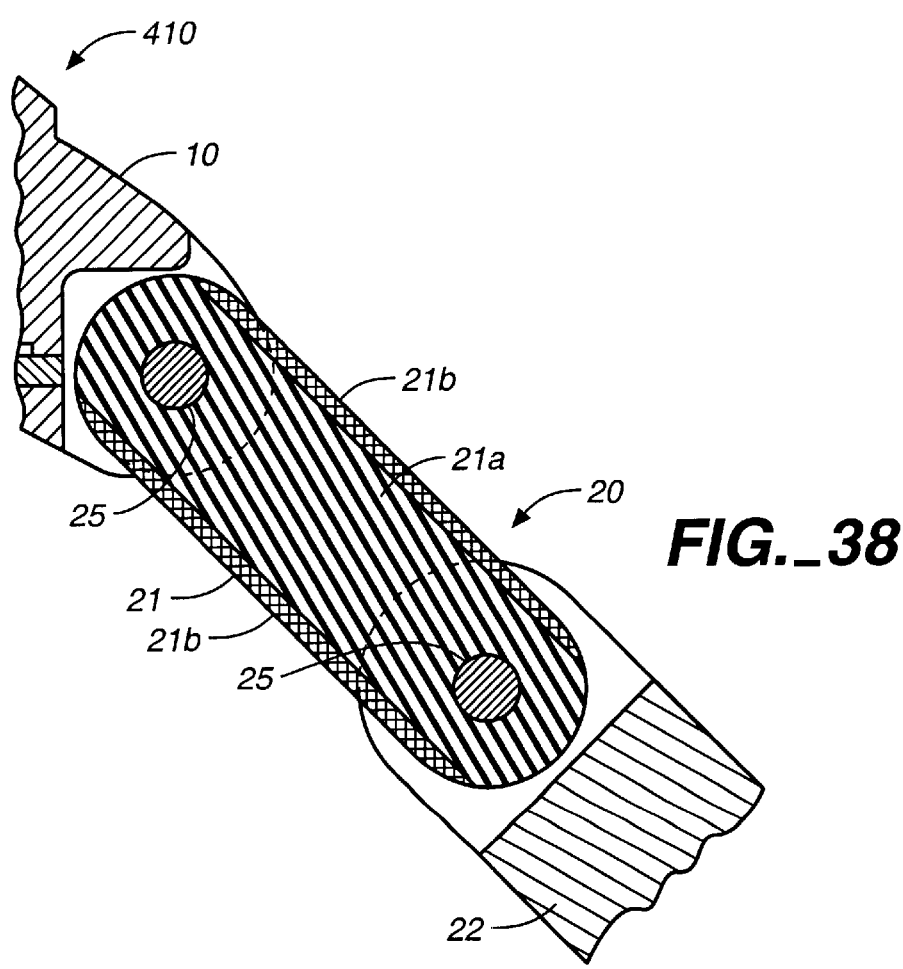
FIG._38

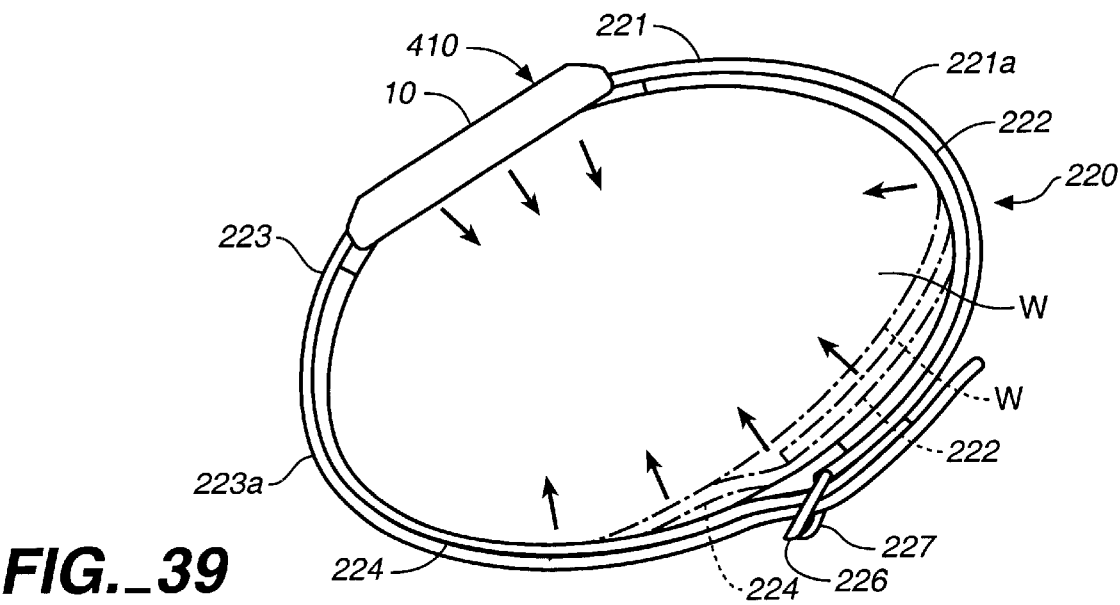
FIG._39
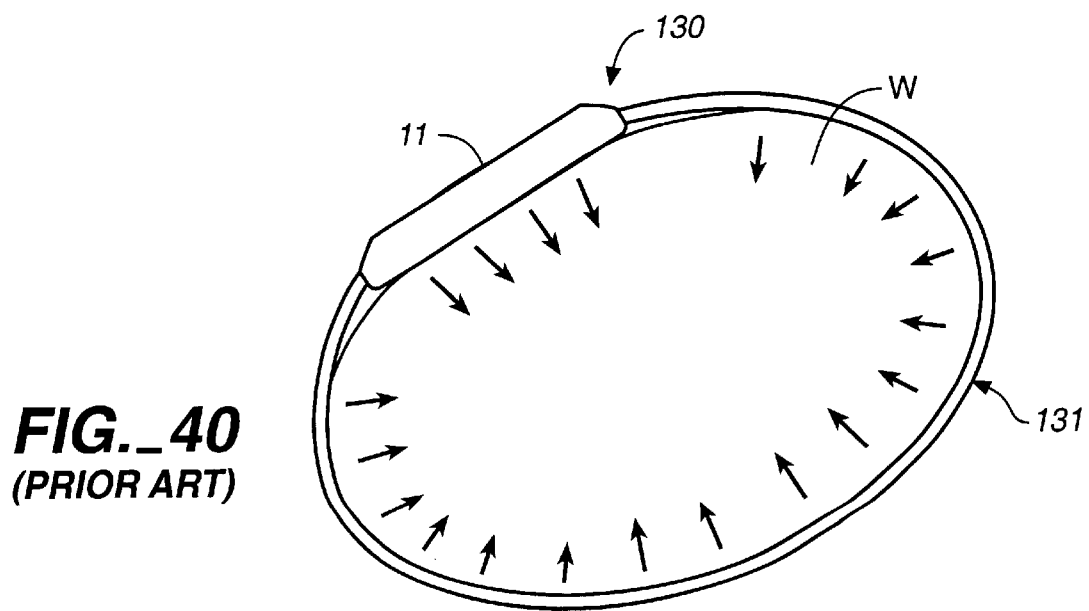
FIG._40
*(PRIOR ART)*

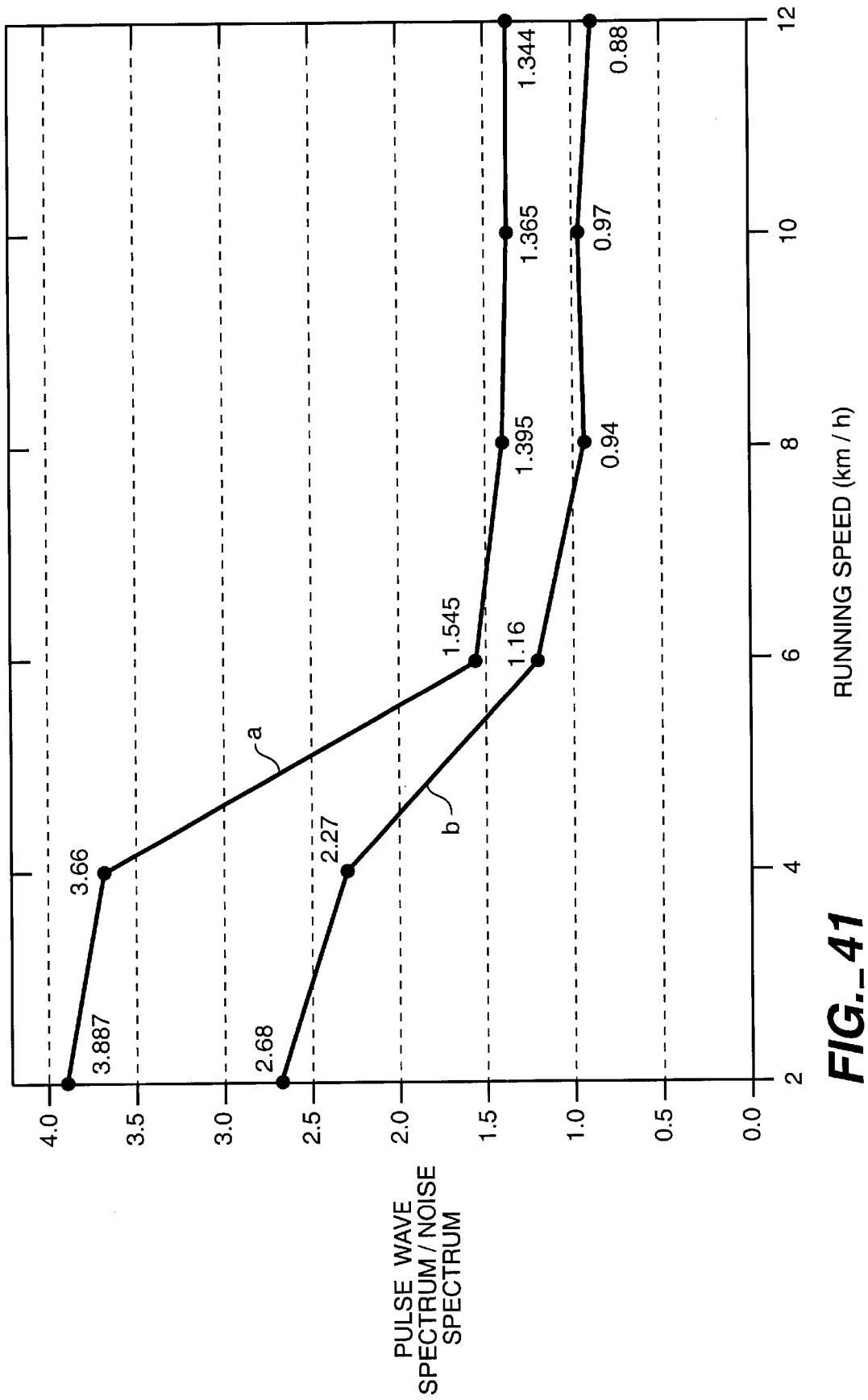
FIG._41

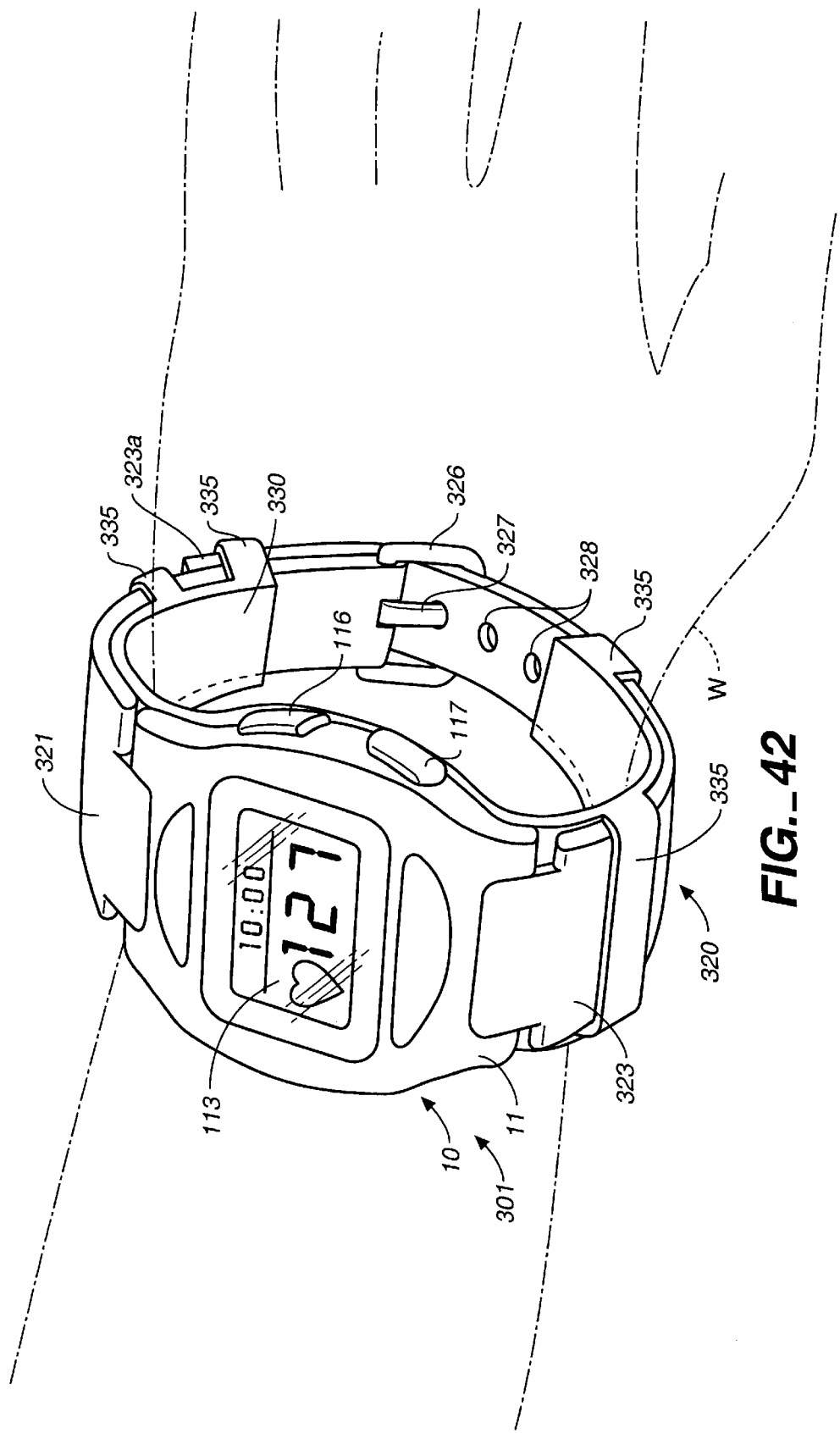

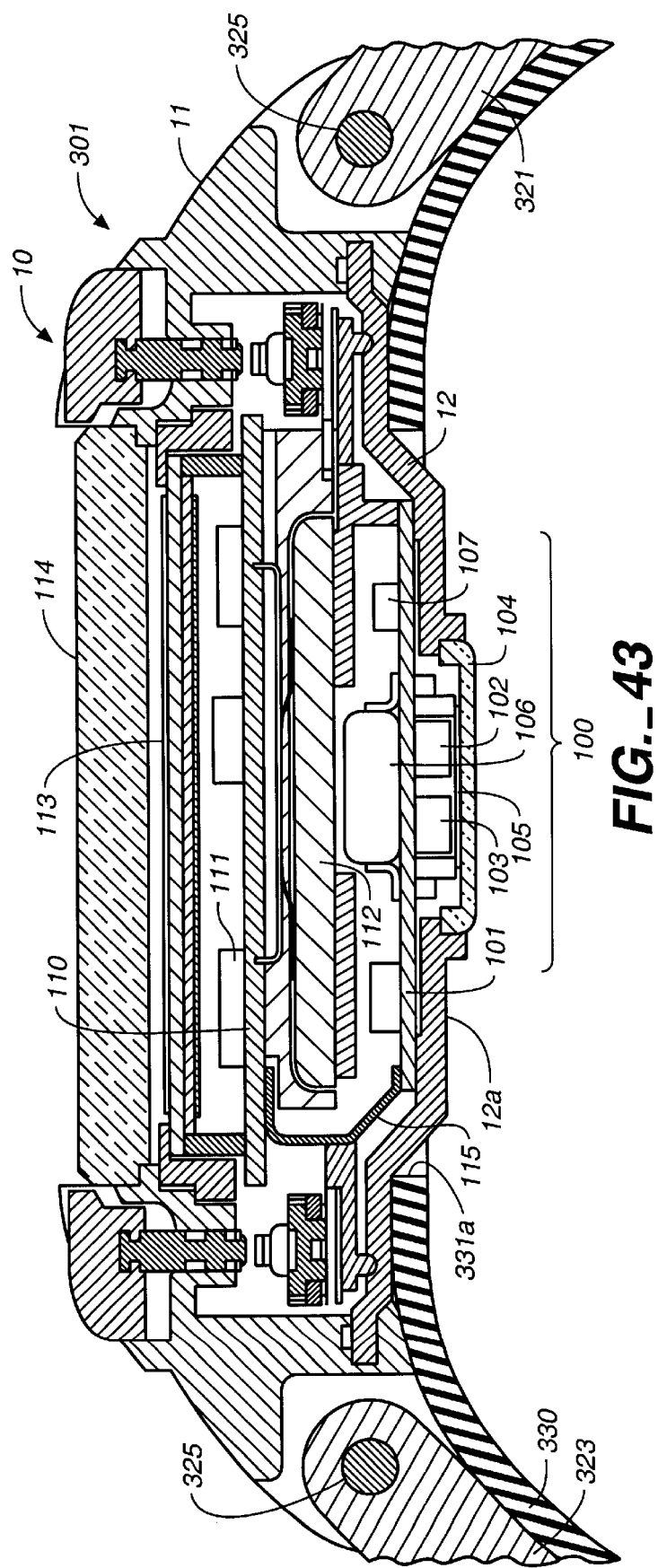
FIG._43

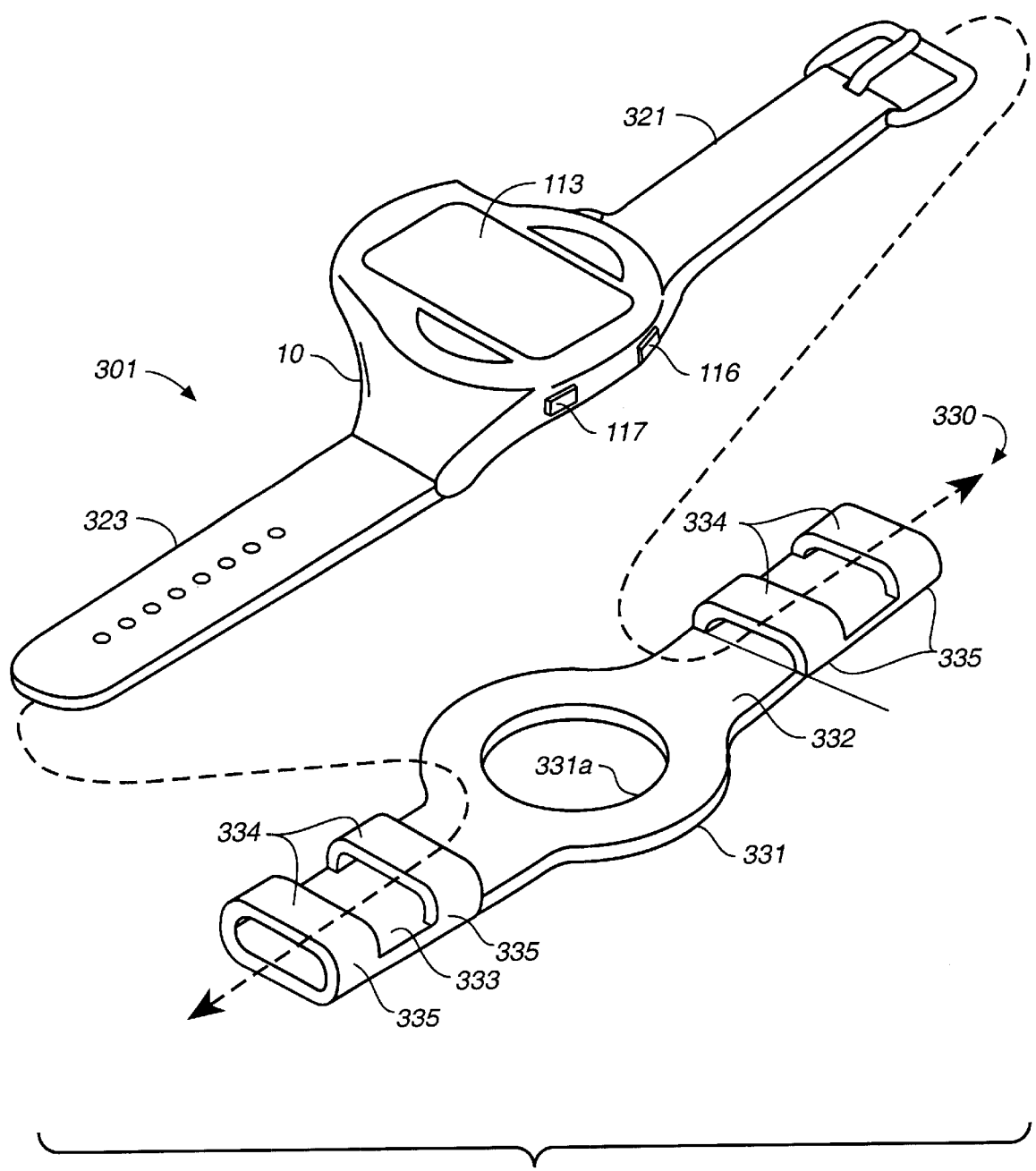
FIG._44

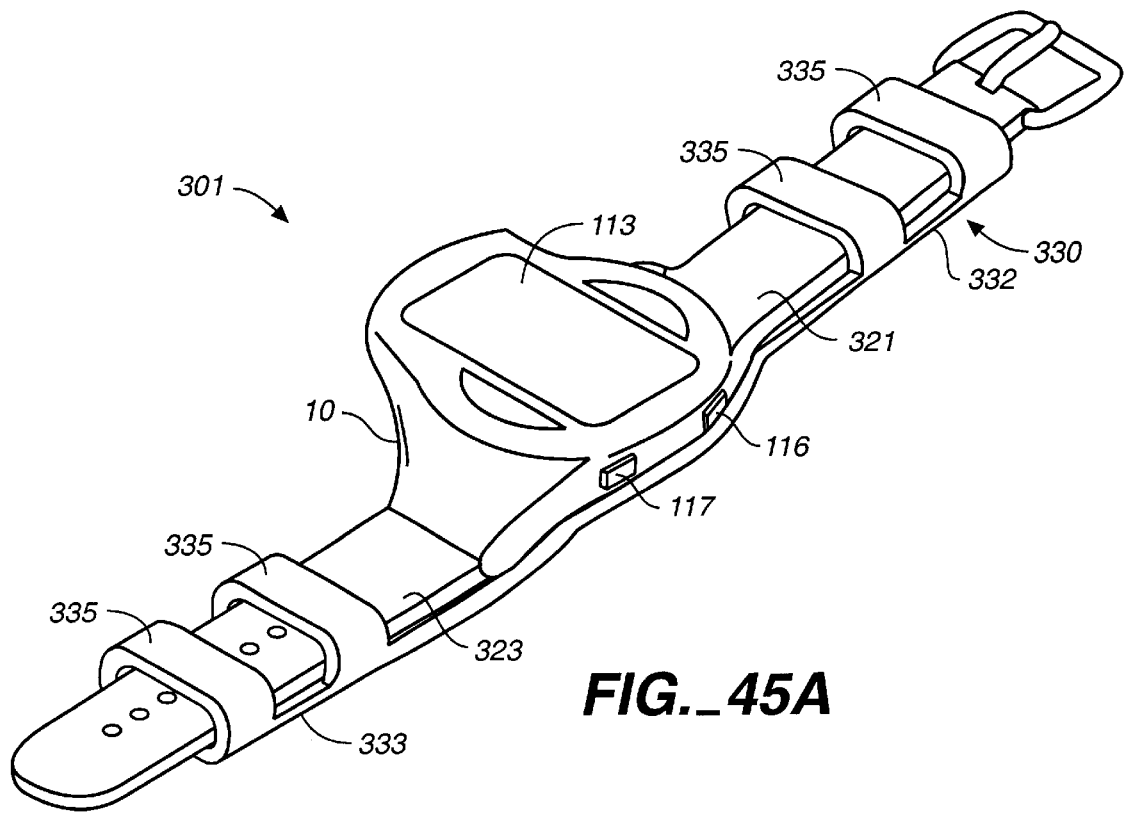
FIG._45A
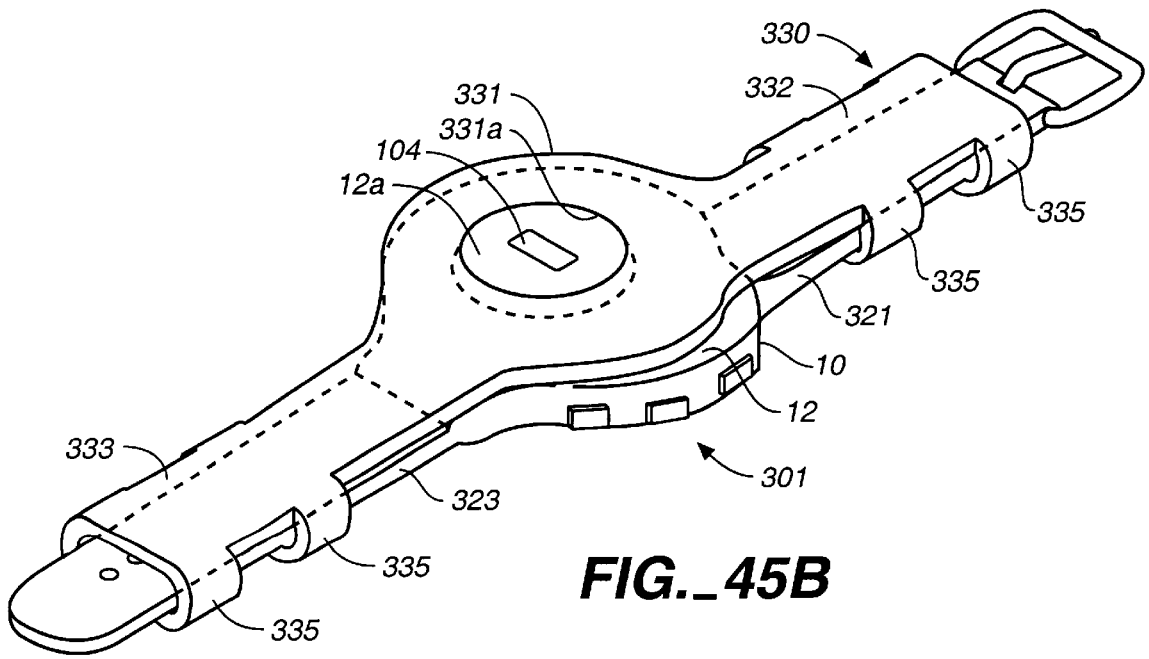
FIG._45B

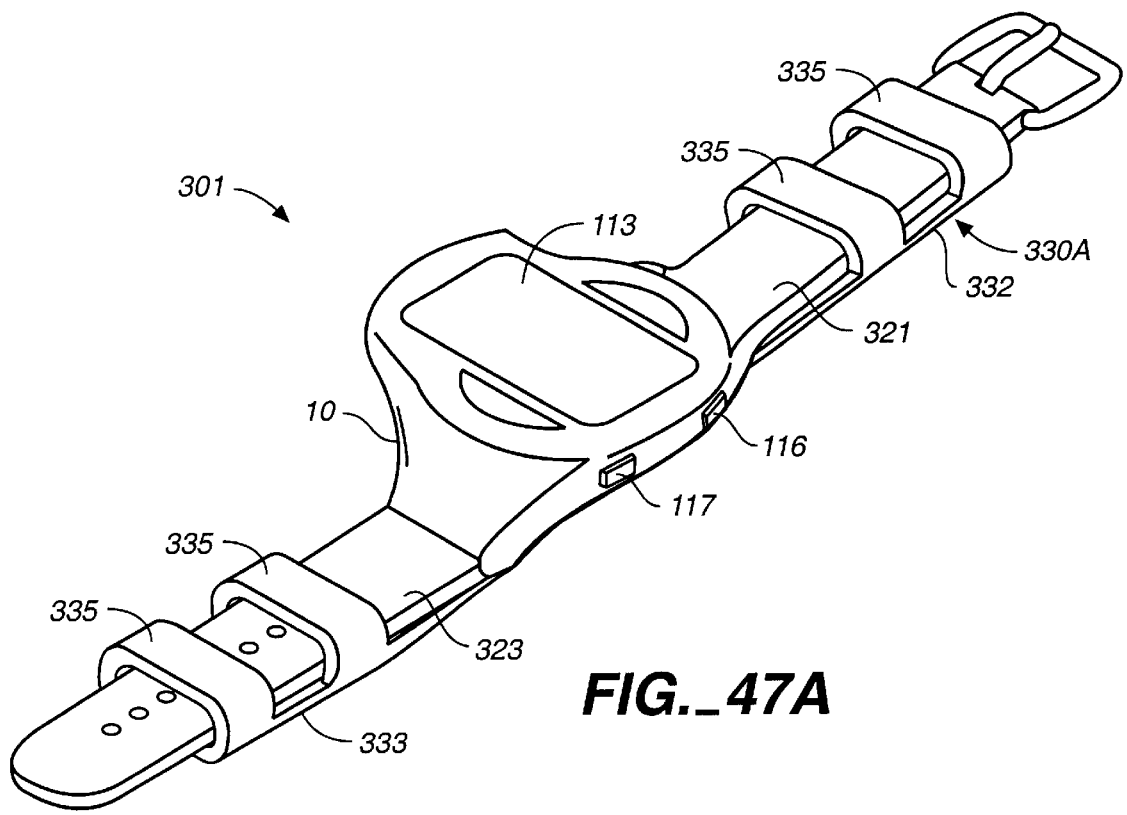
FIG._47A
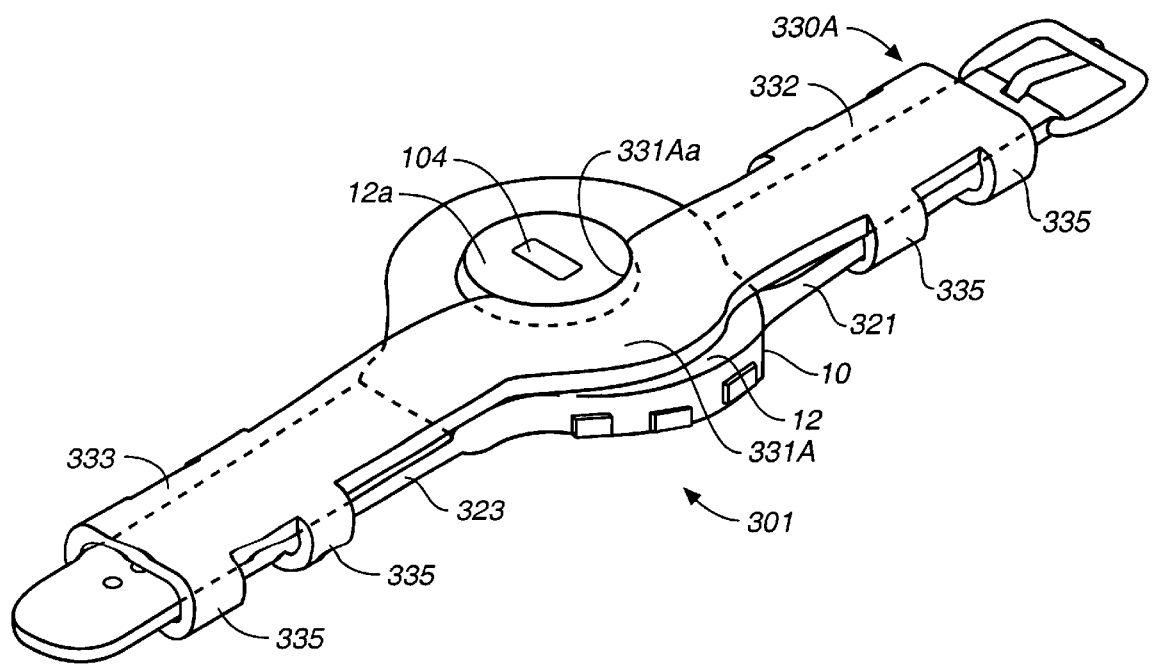
FIG._47B

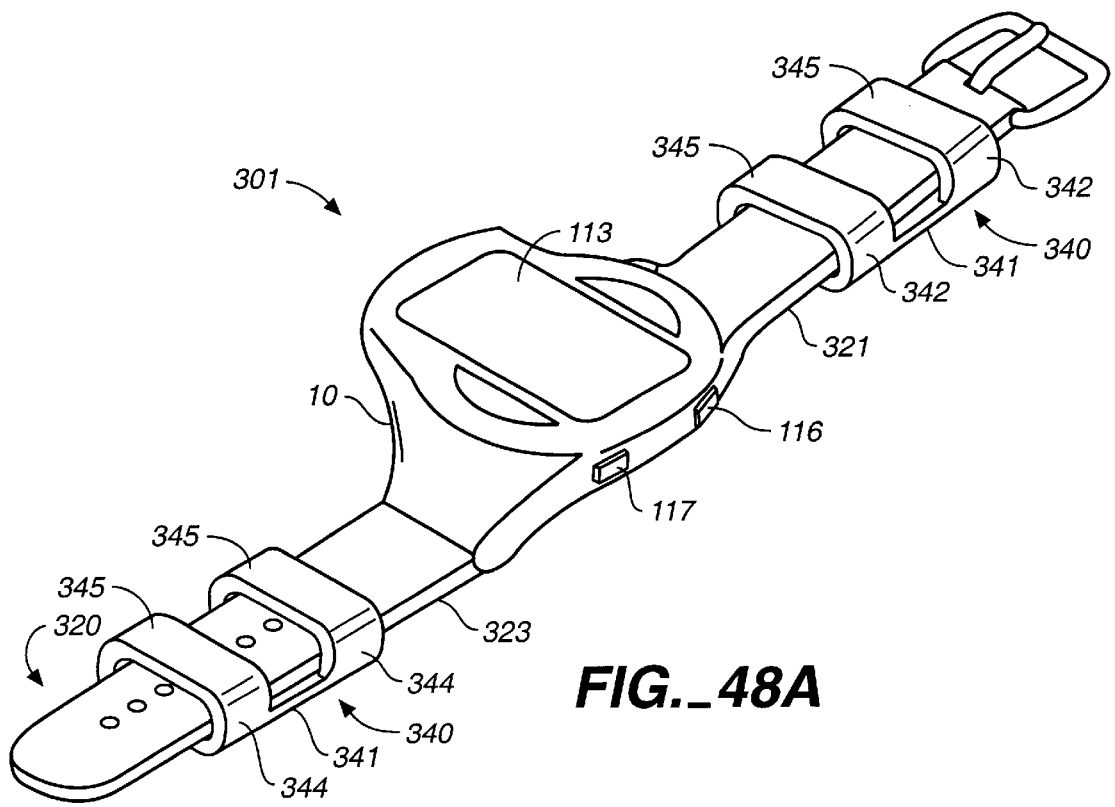
FIG._48A
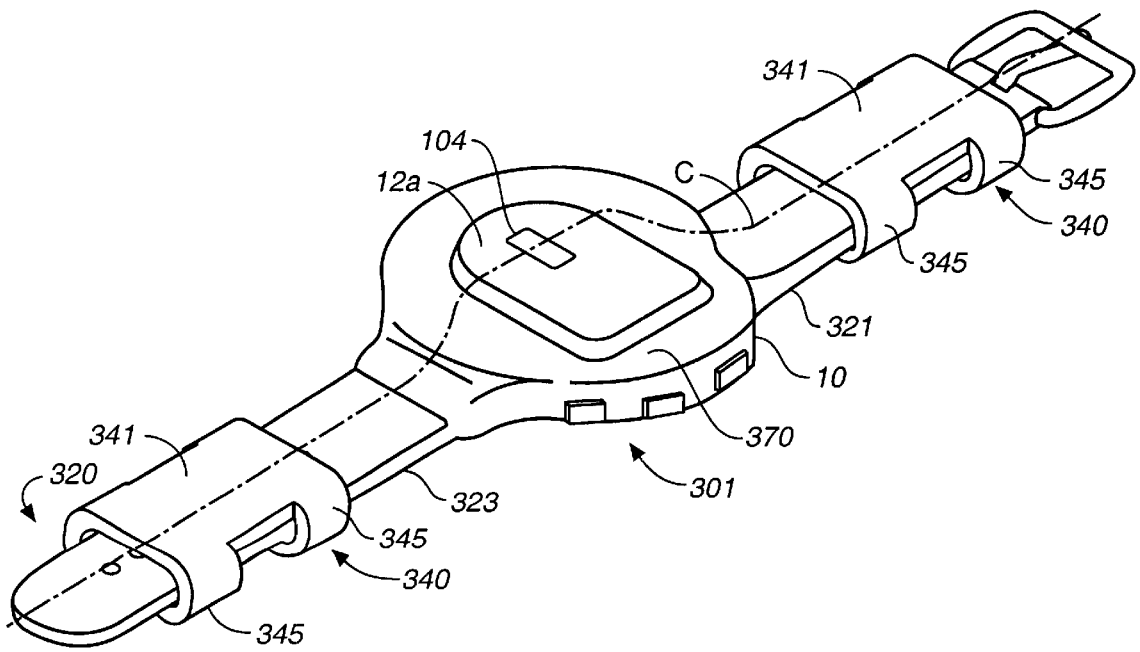
FIG._48B

BIOMETRIC MEASURING DEVICE

TECHNICAL FIELD

The present invention relates to a biometric measuring device having a shape similar to that of a wristwatch and capable of optically measuring biometric information, such as pulse rate, and more particularly, the present invention relates to an improved band for fixing the device to a living body.

BACKGROUND ART

In order to obtain information, such as pulse rate, from a living body, a technique for applying light on the living body and measuring fluctuations of reflected light has already been put into practice. Techniques for pressing and fixing an optically-measuring sensor unit to a surface of a living body, such as a finger surface or a wrist surface, include a technique disclosed in Japanese Unexamined Patent Publication No. 9-108191, which is an application of the present inventors. According to this technique, a circumferentially elastic single supporter-like band is used. This technique is suitable for fixing a sensor unit of small size to a human fingertip.

However, the above-described technique has the following problems.

First, when a sensor unit larger than a sensor unit that can be fitted on a finger, is attached to, for example, a wrist, a large force for holding the weight of the sensor is required for a band. In particular, when an optical sensor unit is used, in order to prevent measurement errors caused by external light, high adherence is required so that a gap is not formed between the sensor unit and the surface of the living body.

In addition, at an easily twisted site, such as a wrist, since a gap is particularly easy to form between the sensor unit and the surface of the living body, the holding force required is excessive. For this reason, the force for pressing the living body must be necessarily increased. This allows the living body to feel high sensation of pressure, and it is therefore difficult to use such a sensor unit for a long time.

The present invention was achieved in consideration of the foregoing circumstances, and an object thereof is to provide a biometric measuring device capable of being mounted on a measurement site of a living body with high adhesion while minimizing the sensation of pressure.

DISCLOSURE OF INVENTION

A biometric measuring device according to the present invention includes a light-emitting means (or light-emitting body) for applying light to a living body; a biometric information detection means (or light-receiving body) for receiving reflected light from the living body of the light applied by the light-emitting means (or light-emitting body) to produce a biometric information signal according to the amount of light received; a support body for supporting the light-emitting means (or light-emitting body) and the biometric information detection means (or light-receiving body); and a band connected to the support body and wound around the living body near the detection site to fix the support body to the living body. Further, according to the present invention, the band is formed of a circumferentially flexible material, and flexibility thereof partially varies in the circumferential direction. In the device according to the present invention, movement, such as twisting of a living body, is permitted by a portion of the band having high flexibility, and holding ability against the living body can be secured by a portion having low flexibility. Therefore, it is possible to mount the device on a measurement site of a living body with high adhesion while minimizing sensation of pressure, and measuring accuracy of the biometric measuring device is improved.

In addition, according to the present invention, the band may have a base material wound around the living body; and an elastic member disposed inside of the base material and having the flexibility higher than that of the base material.

In this case, the base material of the band is wound around the living body together with the support body, whereby the device is mounted on the living body. The holding ability against the living body can be secured by the base material having low flexibility and at the same time, movement, such as twisting of the living body can be permitted by the elastic member disposed inside the base material. Therefore, it is possible to mount the device on the measurement site of the living body with high adhesion while minimizing sensation of pressure, and measuring accuracy of the biometric measuring device is improved.

BRIEF DESCRIPTION OF THE DRAWINGS

The above and other advantages of the present invention will be apparent from the following description of various embodiments of the present invention and the accompanying drawings. In the accompanying drawings, FIG. 1 is a perspective view showing a biometric measuring device according to a first embodiment of the present invention.

FIG. 2 is a plan view showing a connected portion of a housing and a band in the biometric measuring device shown in FIG. 1.

FIG. 3 is a sectional view of the biometric measuring device shown in FIG. 1.

FIG. 4 is a perspective view showing the back side of the biometric measuring device shown in FIG. 1.

FIG. 5 is a circuit diagram showing details of a pulse wave sensor unit of the biometric measuring device.

FIG. 6 is a diagram showing a principle of measurement of a pulse wave by the biometric measuring device shown in FIG. 1.

FIG. 7 is a diagram showing fluctuations in absorbance with time when light is applied to a part including a human capillary from the outside.

FIG. 8 is a graph showing a blood pressure distribution of a human body.

FIG. 9 is a functional block diagram of a data processing circuit for processing an output signal of the pulse wave sensor unit shown in FIG. 1.

FIG. 10 is a sectional view of band pieces constituting a band of the biometric measuring device shown in FIG. 1.

FIG. 11 is a diagram showing a conventional biometric measuring device attached to a human wrist.

FIG. 12 is a diagram showing the biometric measuring device of the first embodiment shown in FIG. 1 that is attached to a human wrist.

FIG. 13 is a perspective view showing a biometric measuring device according to a second embodiment of the present invention.

FIG. 14 is a perspective view showing a biometric measuring device according to a third embodiment of the present invention.

FIG. 15 is a perspective view showing a biometric measuring device according to a fourth embodiment of the present invention.

FIG. 16 is a perspective view showing a biometric measuring device according to a fifth embodiment of the present invention.

FIG. 17 is a perspective view showing a biometric measuring device according to a sixth embodiment of the present invention.

FIG. 18 is a perspective view showing a biometric measuring device according to a seventh embodiment of the present invention.

FIG. 19 is a plan view showing a connected portion of a housing and a band in the biometric measuring device shown in FIG. 1;.

FIG. 20 is a sectional view of the biometric measuring device shown in FIG. 18.

FIG. 21 is a perspective view showing the back side of the biometric measuring device shown in FIG. 18.

FIG. 22 is a side view showing the biometric measuring device shown in FIG. 18 that is attached to a wrist of a test subject.

FIG. 23 is an exploded perspective view of a base material and an elastic body for the representation of one method for attaching the base material to the elastic member of the above band.

FIG. 24 is an exploded perspective view of a base material and an elastic body for the representation of another method for attaching the base material and the elastic member of the above band.

FIG. 25 is a perspective view showing a band piece to which the base material and the elastic body are attached by the method of FIG. 24.

FIG. 26 is an exploded perspective view of a base material and an elastic body for the representation of another method for attaching the base material and the elastic member of the above band.

FIG. 27 is a perspective view showing a band piece to which the base material and the elastic body are attached by the method of FIG. 26.

FIG. 28 is an exploded perspective view of base materials and elastic bodies for the representation of another method for attaching the base materials and the elastic members of the above band.

FIGS. 29A and 29B are perspective view each showing the biometric measuring device to which the base materials and the elastic bodies are attached by the method of FIG. 28.

FIG. 30A is a perspective view showing the vicinity of a connected portion of band pieces in the biometric measuring device in accordance with the method of FIG. 28.

FIG. 30B is a side view of the vicinity of the connected portion shown in FIG. 30A.

FIG. 31 is a side view showing a biometric measuring device according to a modification that is attached to a wrist of a test subject.

FIG. 32 is a front view showing a biometric measuring device according to an improvement example.

FIG. 33 is shows an overall configuration of a pulse-measuring device that is a biometric measuring device according to an eighth embodiment of the present invention.

FIG. 34 is a sectional view showing a finger-fitting unit of the pulse-measuring device shown in FIG. 33.

FIG. 35 is a plan view showing the finger-fitting unit shown in FIG. 34.

FIGS. 36A and 36B are diagrams for the explanation of a superior effect, obtained by the pulse-measuring device shown in FIG. 33.

FIG. 37 is a side view showing a device main body of the pulse-measuring device shown in FIG. 33.

FIG. 38 is a partial sectional view of a wristband used in the pulse-measuring, device shown in FIG. 33.

FIG. 39 is a side view showing a device main body of a pulse-measuring device according to a modification of the eighth embodiment.

FIG. 40 is a side view showing a device main body of a conventional pulse-measuring device attached to a wrist of a test subject.

FIG. 41 is a graph for the explanation of the effect of the eighth embodiment.

FIG. 42 is a perspective view showing an overall configuration of a pulse-measuring device that is a biometric measuring device according to a ninth embodiment of the present invention.

FIG. 43 is a sectional view of the pulse-measuring device shown in FIG. 42.

FIG. 44 is an exploded perspective view of a pulse-measuring device and an elastic member for the representation of a method for attaching the pulse-measuring device and the elastic member shown in FIG. 42.

FIGS. 45A and 45B are perspective views each showing the pulse-measuring device to which the elastic member is attached by the method of FIG. 44.

FIGS. 47A and 47B are perspective view each showing a pulse-measuring device according to a modification of the ninth embodiment.

FIGS. 48A and 48B are perspective views each showing a pulse-measuring device according to a tenth embodiment.

BEST MODE FOR CARRYING OUT THE INVENTION

First Embodiment (1) Schematic Configuration

Figure 46:
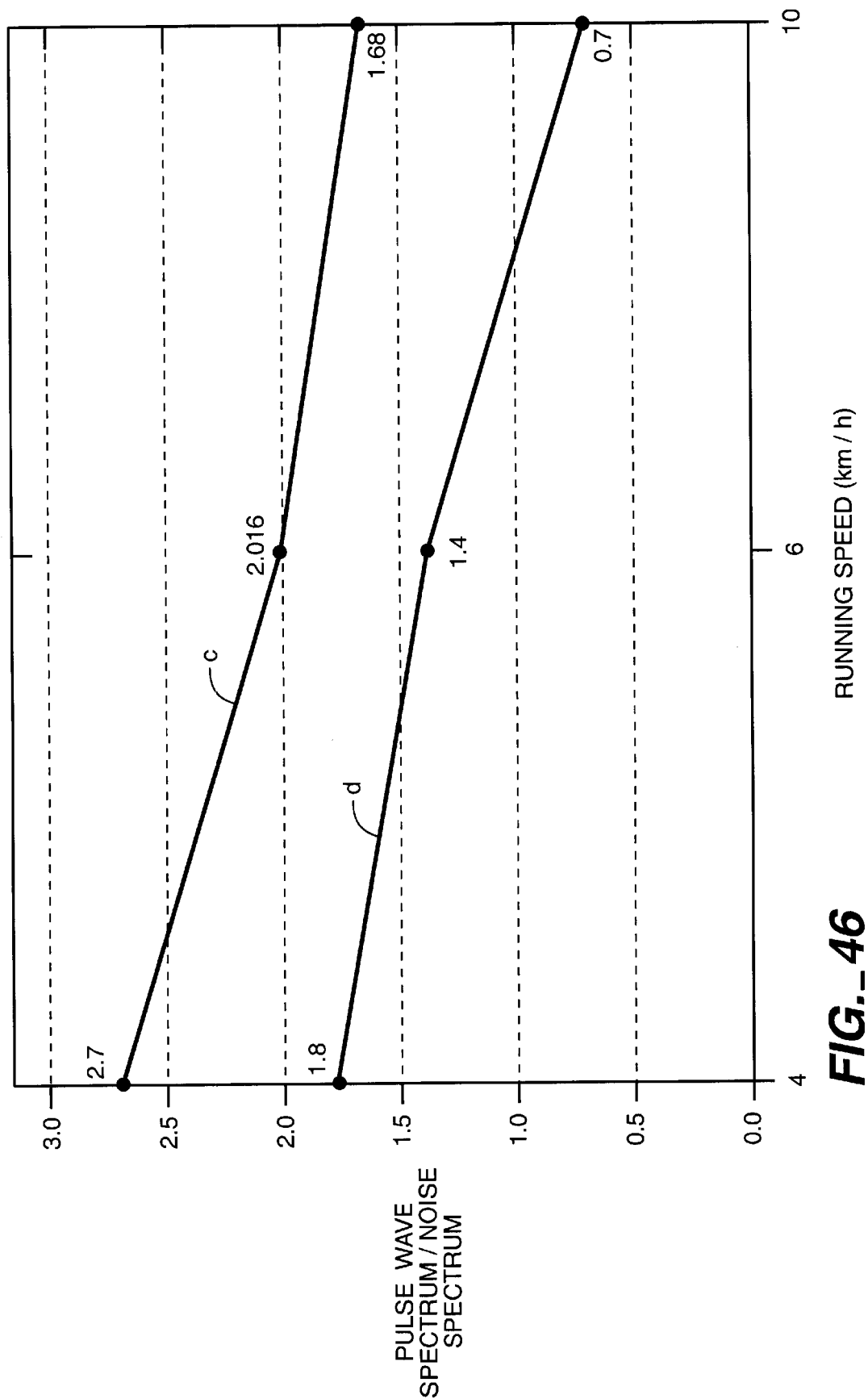
FIG. 46 is a graph for the explanation of the effect of the ninth embodiment.

As shown in FIG. 1, a biometric measuring device of the first embodiment according to the present invention is of a wristwatch type which includes a housing (support body) 10 storing therein various electrical or electronic parts, and a wristband 20 connected to the housing 10 and wound around a human arm to fix the housing 10 to the arm.

The wristband 20 of this embodiment has four band pieces 21 to 24. A short band piece 21 is connected to the upper end of the housing 10 at one end thereof, and is connected to one end of a long band piece 22 at the other end thereof. As shown in FIG. 2, the connection method is a well-known method using spring rods 25. Returning to FIG. 1, a buckle 26 and a tongue 27 are attached by a well-known method to the other end of the band piece 22 that is farther away from the housing 10.

In addition, another short band piece 23 is connected to the lower end of the housing at one end thereof, and is connected to one end of a long band piece 24 at the other end thereof The connection method is similar to that shown in FIG. 2. Plural small holes 28 are formed in the band piece 24 at equal intervals along the longitudinal direction thereof The band piece 24 is inserted into the buckle 26 and the tongue 27 is put through any one of the small holes 28, whereby the biometric measuring device is fixed to a human arm, and the back of the housing 10 is brought into tight contact with the back of the wrist. By selecting the small hole 28 through which the tongue 27 is inserted, the perimeter of the device is adjusted. Details of the wristband 20 will be described hereinbelow.

FIG. 3 shows a cross section of the housing 10. As shown in the figure, the housing 10 has an outer casing 11 disposed on the front side and a back cover 12 disposed on the back side. The outer casing 11 and the back cover 12 are fixed in combination with each other, and a space for accommodating therein various electric or electronic parts is formed therein. As materials for the outer casing 11 and the back cover 12, lightproof materials are selected.

A pulse wave sensor unit 100 is supported on the housing 10. The pulse wave sensor unit 100 is a reflective optical sensor, and has a circuit board 101 disposed on the back cover 12, an LED (Light Emitting Device) 102 which is a light-emitting body mounted on the back of the circuit board 101, and a photodiode 103 which is a light-receiving body. Light emitted from the LED 102 travels downward in the figure to illuminate the wrist of a person who has the device mounted thereon. The illumination light is absorbed by tissues or blood vessels of the wrist, and the illumination light which is not absorbed is reflected. The reflected light is received by the photodiode 103, and the photodiode 103 generates an electric signal corresponding to the intensity of the light received.

A through hole is formed in the center of the back cover 12, and a transparent glass 104 is fixed so as to cover the through hole. The transparent glass 104 permits transmission of light for the LED 102 and the photodiode 103 and at the same time, protects them. In addition, a light filter 105 is disposed between the transparent glass 104 and the LED 102, and the photodiode 103. Therefore, the illumination light from the LED 102 passes through the light filter 105 to illuminate the wrist, and the reflected light passes through the light filter 105 to be received by the photodiode 103. The layout of the LED 102, photodiode 103, and transparent glass 104 is also shown in FIG. 4.

The light filter 105 transmits light beams in a wavelength range of 500 nm to 600 nm. The measurement wavelength of the measurement optical system is within the range of 500 nm to 600 nm. The present inventors and joint researchers have found that, by wavelengths in this range, pulse waves can be measured with the highest accuracy when arterioles of the wrist are the measured objects.

An OP amplifier 106 and a circuit element 107 are mounted on the front side of the circuit board. The OP amplifier 106 amplifies an electric signal output from the photodiode 103. The circuit element 107 is provided with resistors 107a and described below 107b and the like that are connected to the OP amplifier 106 and the LED 102.

In addition, a main substrate 110 is disposed in the internal space of the housing 10. The main substrate 110 is provided with a data processing circuit 111 including an IC component, such as a CPU (central processing unit). A battery 112 serving as a power source of the biometric measuring device is disposed on the back side of the main substrate 110, and the battery 112 is connected to a circuit provided on the main substrate 110. Furthermore, a liquid crystal display device 113 is disposed on the front side of the main substrate 110. A transparent glass 114 for enabling the liquid crystal display device 113 to be viewed and protecting the liquid crystal display device 113 is disposed on the front side of the liquid crystal display device 113, and the transparent glass 114 is supported by the outer casing 11 of the housing 10. The pulse rate (biometric information measured in this embodiment), which is a measurement result of the pulse wave sensor unit 100, is displayed on the liquid crystal display device 113.

In addition, in this embodiment, the circuit provided on the main substrate 110 has the function of counting time and date, in a manner similar to a common digital watch. The liquid crystal display device 113 can also display the time and date in addition to the above-described pulse rate. In the liquid crystal display device 113 shown in FIG. 1, "10:08" represents the time, and "127" represents the pulse rate. As shown in FIG. 1, the outer casing 11 of the housing 10 is provided. with button switches 116 and 117 for setting the time or switching display modes.

As shown in FIG. 3, the above-described main substrate 110 and the pulse wave sensor unit 100 are connected to each other by a heat seal 115. This allows electric power to be supplied from the main substrate 110 to the pulse wave sensor unit 100, and allows a pulse wave signal to be supplied from the pulse wave sensor unit 100 to the main substrate 110.

(2) Pulse Detection

FIG. 5 shows details of the pulse wave sensor unit 100. As shown in the figure, the positive voltage +V is given to an anode of the LED 102, and a cathode thereof is grounded via the resistor 107a. Since the resistor 107a acts as an electric current-restricting resistor, desired electric current flows through the LED 102.

In addition, the positive voltage +V is given to a cathode of the photodiode 103, and an anode is connected to a negative input terminal of the OP amplifier 106. An output signal of the OP amplifier 106 is fed back to the negative input terminal via the resistance 107b. Input impedance of the OP amplifier 106 is extremely high, and the gain is large.

In addition, since a positive input terminal of the OP amplifier 106 is grounded, an anode of the photodiode 103 is subjected to an imaginary short-circuit to the ground. Therefore, the photodiode 103 is reverse biased, and when light is incident thereon, electric current according to the amount of light flows. The greater the intensity of the incident light, the larger the current which flows. The OP amplifier 106 and the resistance 107b convert the electric current from the photodiode 103 into voltage, and amplify the voltage. That is, an output signal Vm of the OP amplifier 106 varies with the amount of the incident light.

A principle of the pulse wave sensor unit 100 will be described with reference to FIG. 6. In the figure, T represents a skin of a living body to be detected, and C represents a capillary and an arteriole. There is living tissue between the skin T and the capillary C. Blood flows through the capillary C.

A part of the light illuminated from the LED 102 is absorbed by the tissues of the living body or hemoglobin in the blood, another part of the light is reflected by the tissue of the living body, and the reflected light is received by the photodiode 103. The photodiode 103 outputs an electric signal according to the amount of the light received. Therefore, the absorption by the tissues of the living body and the absorption by the hemoglobin in the blood are reflected in the output signal of the photodiode 103.

FIG. 7 is a diagram showing fluctuations in absorbance when light is illuminated on a human capillary from the outside, in which $I_2$ is an absorption component based on the tissue, $I_3$ is an absorption component based on venous blood, and $I_4$ is an absorption component based on arterial blood. The absorption component $I_2$ based on the tissue is fixed because tissue density does not change. In addition, the absorption component $I_3$ based on venous blood is also fixed. This is because there is no pulsation or density variation in the vein.

As shown in FIG. 8, blood pressure according to pulsation of blood delivered from a heart is generally high and greatly fluctuates in the capillary, which is nearer to the heart, and no fluctuation occurs in the vein. Therefore, the output electric current of the photodiode 103 fluctuates with the pulsation of the artery. Thus, the output signal Vm of the OP amplifier 106 obtained by amplifying the output of the photodiode 103 can be regarded as a pulse wave signal. That is, according to this embodiment, the pulse wave is measured from bloodflow fluctuations in the arteries and arterioles of the wrist (particularly, the arterioles near the back of the wrist).

FIG. 9 is a functional block diagram of the data processing circuit 111 of the main substrate 110. The pulse wave signal Vm produced in the pulse wave sensor unit 100 is supplied to a pulse wave signal conversion part 120, and the pulse wave signal conversion part 120 converts the pulse wave signal Vm from an analog signal to a digital signal (pulse wave data MD). The pulse wave data MD is transferred to a storage part 121, such as a RAM (random access memory), and the storage part 121 temporarily stores the pulse wave data MD produced in a predetermined period.

The pulse wave data MD is read from the storage part 121 with a constant period, and the read pulse wave data MD is transferred to a frequency analysis part 122. The frequency analysis part 122 analyzes the frequency of the pulse wave data MD to produce pulse wave analysis data MKD. While various methods may be used as the frequency analysis, FFT (fast Fourier transform) is used in this embodiment so that the frequency can be analyzed in a short calculation time.

Next, the pulse wave analysis data MKD is supplied to a pulse rate calculation part 123, and the pulse rate calculation part 123 calculates the pulse rate HR based on the pulse wave analysis data MKD. In the calculation, the pulse rate calculation part 123 specifies peaks of spectrum intensity of the pulse wave analysis data MKD, measures a time interval between the peaks, and calculates the frequency Fh based on the time interval. Since the frequency Fh is a fundamental frequency of the pulse wave signal Vm, the pulse rate calculation section 58 calculates the pulse rate HR, which is a pulse rate per one minute, by the following equation.

$$HR = 60Fh$$

When the SN ratio of the pulse wave signal Vm is sufficiently high, however, the pulse wave signal Vm may be simply subjected to waveform shaping to be converted to a rectangular wave instead of the frequency analysis, and a period of the rectangular wave may be obtained so as to display the pulse rate HR.

The pulse rate HR calculated by either one of the above methods is displayed on the liquid crystal display device 13. The pulse of a test subject is made known in this way.

(3) Details of Wristband

The wristband 20 for winding the biometric measuring device around the wrist of the test subject consists of four band pieces 21 to 24, as described above. The short band pieces 21 and 24 near the housing 10 are formed of a material having high flexibility, while the long band pieces 22 and 24 far from the housing 10 are formed of a material having low flexibility. FIG. 10 shows cross sections of the band piece 21 and the band piece 22.

As shown in FIG. 10, the band piece 21 consists of a central layer 21a, and fiber textile layers 21b secured to both sides thereof The central layer 21a is formed of a material having high elasticity, such as urethane foam rubber or polyurethane rubber, and the fiber textile layer 21b is formed of textile that can follow expansion and contraction of the central layer 21a. Although it is not shown in the figure, the band piece 23 has a similar configuration.

On the other hand, the band piece 22 is formed of plastic having low elasticity, such as urethane, or of silicone, in a uniform density. Although it is not shown in the figure, the band piece 24 has a similar configuration. As materials for the above band pieces 21 to 24, lightproof materials are selected in order to minimize measurement errors of the pulse wave sensor unit 100, which is an optical sensor.

The flexibility of the wristband 20 partially varies in the circumferential direction due to the difference in materials of the above band pieces 21 to 24. According to the wristband 20, movement, such as twisting of the wrist, is permitted by portions of the band having high flexibility (short band pieces 21 and 23), and the holding ability against the living body can be secured by portions having low flexibility (long band pieces 22 and 24). This effect will be described with reference to FIGS. 11 and 12.

FIG. 11 shows a biometric measuring device having a conventional wristband 30 which is attached to a wrist W of the test subject, is formed of a single member, and has circumferentially uniform flexibility. According to this conventional art, substantially uniform pressure is applied to a portion where the housing 10 is in contact with the wristband 20. If the pressure is weak, however, the housing 10 may separate from the wrist W, as shown by an imaginary line in FIG. 11, when the test subject moves an arm (for example, when the wrist W is twisted). In such a case, a gap is formed between the LED 102 and the photodiode 103 of the pulse wave sensor unit 100, and the wrist, and external light enters the gap.

In such a state, the influence of the measurement errors caused by external light cannot be ignored. Since the wrist is a site that is easily twisted, this problem tends to occur when the test subject moves. On the other hand, if the pressure is strong, the separation of the wrist W and the housing 10 can be prevented. However, since the living body necessarily feels strong sensation of pressure, it is difficult to use the device for a long time.

FIG. 12 shows the biometric measuring device having the wristband 20 of the above embodiment attached to the wrist W of the test subject. According to this embodiment, the wrist W receives high pressure from the band pieces 22 and 24 and the housing 10 having low flexibility, while the wrist W does not receive too high a pressure from the band pieces 21 and 23 having high flexibility. Moreover, since the band pieces 21 and 23 located near the housing 10 supporting the pulse wave sensor unit 100 have high flexibility, they easily expand and contract following movement of the arm, and the housing 10 is difficult to separate from the wrist W. Therefore, the pulse wave sensor unit 100 resists the influence of the external light, and occurrence of measurement errors can be reduced.

On the other hand, the force for supporting the wrist W is secured by the band pieces 22 and 24 far from the housing 10, and by the housing 10. In other words, movement of a living body, such as twisting, is permitted by the band pieces 21 and 23 of the band 20 having high flexibility, and holding ability against a living body can be secured by the band pieces 22 and 24 having low flexibility. Therefore, it is possible to mount the biometric measuring device on a measurement site of the living body with high adhesion while minimizing the sensation of pressure given to the living body, and measuring accuracy of the biometric measuring device is improved.

In addition, according to the wristband 20 of this embodiment, since a perimeter adjusting mechanism is formed by the buckle 26, the tongue 27 and the small holes 28, it is not necessary to prepare various types of bands even if the device is mounted to a site substantially varying in size among individuals, such as the human wrist, as compared with the conventional wristband 30 consisting of a single member. Therefore, it is possible to measure a number of test subjects using one device. Furthermore, the provision of the perimeter adjusting mechanism can allow diversified design variations as compared with the conventional wristband 30 consisting of a single member.

Second Embodiment

FIG. 13 shows a biometric measuring device of the second embodiment according to the present invention. According to this device, two band pieces 21A and 23A of a wristband 20 near a housing 10 are formed of a member having high mechanical flexibility. This allows the band pieces 21A and 23A to have flexibility in the circumference direction higher than band pieces 22 and 24 far from the housing 10. Other points are similar to those of the first embodiment.

More specifically, at least one of a mesh made by twisting slender components having high elasticity, a coil spring made of a linear component having, high elasticity, or a component made by combining a plurality of links and allowed to be flexible by a spring, is provided at least in the middle of band pieces 21A and 23A. In this way, the flexibility of the band pieces 21A and 23A is mechanically increased. Furthermore, in order to eliminate the influence of external light on measurement as much as possible, a member for increasing light-shielding capability of the band pieces 21A and 23A, such as a rubber plate, may be attached to the back side of the band pieces 21A and 23A.

The technique for mechanically increasing the flexibility in this way may be applied to fourth to sixth embodiments described hereinbelow.

Third Embodiment

FIG. 14 shows a biometric measuring device of the third embodiment, according to the present invention. According to this device, a wristband 20 has two band pieces 21B and 23B. The band pieces 21B and 23B are connected to the upper end and the lower end of a housing 10, respectively, and are connected to each other by a buckle 26, a tongue 27, and small holes 28. The connection method to the housing 10 is similar to that shown in FIG. 2.

The band pieces 21B and 23B have a layer structure similar to that of the band piece 21 shown in FIG. 10, or have a structure similar to a flexible textile for use in an athletic supporter. However, the thickness of the band pieces 21B and 23B increases as they separate from the housing 10. This allows the flexibility of the wristband 20 to vary partially in the circumferential direction. According to the wristband 20, movement of an arm, such as twisting of a wrist, is permitted by portions of the band having high flexibility (portions near the housing 10), holding ability against a living body can be secured by portions having low flexibility (portions far from the housing 10), and measuring accuracy of the biometric measuring device can improved. The technique for varying the flexibility in the circumferential direction in this way may be applied to fourth to sixth embodiments described hereinbelow.

Fourth Embodiment

FIG. 15 shows a biometric measuring device of the fourth embodiment according to the present invention. According to the device, one band piece 21 having high flexibility in the structure of the first embodiment shown in FIG. 1 is deleted, and a band piece 22A having low flexibility is directly connected to a housing 10 therefor. That is, according to this embodiment, a wristband 20 consists of a band piece 23 having high flexibility, and band pieces 22A and 24 having low flexibility. The connection method of the band piece 24A and the housing 10 is similar to that shown in FIG. 2.

If movement, such as twisting of a wrist, is permitted by a portion of the band having high flexibility (band piece 23), and holding ability against the living body can be secured by portions having low flexibility (band pieces 22A and 24), there is no inconvenience even in this embodiment. In addition, if this effect can be achieved, the band piece 21 may be provided and the band piece 23 may be deleted contrary to the manner shown in the figure. Such a portion having high flexibility may be provided even in one place in the circumferential direction of the band 20.

Fifth Embodiment

FIG. 16 shows a biometric measuring device of the fifth embodiment according to the present invention. According to the device, a wristband 20 has two band pieces 21C and 24C. The band pieces 21C and 24C are connected to the upper end and the lower end of a housing 10, respectively, and are connected to each other by a buckle 26, a tongue 27, and small holes 28. The connection method to the housing 10 is similar to that shown in FIG. 2. The band piece 21C has the flexibility higher than that of the band piece 24C.

In this embodiment, the flexibility of the wristband 20 also varies partially in the circumferential direction. According to the wristband 20, movement of an arm, such as twisting of a wrist, is permitted by a portion of the band having high flexibility (band piece 21C), holding ability against the living body can be secured by a portion having low flexibility (band piece 24C), and measuring accuracy of the biometric measuring device can be improved.

Sixth Embodiment

FIG. 17 shows a biometric measuring device of the sixth embodiment according to the present invention. According to the device, a wristband 20 has four band pieces 21D, 22D, 22E, and 24D. However, the band piece 24D is connected to the lower end of a housing 10 to form a lower part of the band by itself, while an upper part of the band is formed by three band pieces 21D, 22D, and 22E. That is, the band piece 22D is connected to the upper end of the housing 10, and the band piece 21D is connected thereto, and further, the band piece 22E is connected thereto.

The band piece 21D has high flexibility, while other band pieces 22D, 22E, and 24D have the flexibility lower than that of the band piece 21D. Therefore, in the upper part of the band formed by the three band pieces 21D, 22D, and 22E, only a middle portion (band piece 21D) has high flexibility.

As described above, in order to permit movement of an arm, such as twisting of a wrist, and secure holding ability against the living body, it is preferable that the band piece, which is nearer the housing 10, has higher flexibility. However, if such an effect can be achieved, there is no inconvenience even if the flexibility of the portion far from the housing 10 is high as in this embodiment.

Seventh Embodiment (1) Overview of Device

FIG. 18 shows a biometric measuring device of a seventh embodiment according to the present invention. As shown in FIG. 18, the biometric measuring device is also of a wristwatch type which includes a housing (support body) 10 storing therein various electrical or electronic parts, and a wristband 220 connected to the housing 10 and wound around a human arm to fix the housing 10 to the arm.

The wristband 220 in this embodiment has two band pieces 221 and 223. The band piece 221 is connected to the upper end of the housing 10 at one end thereof, and a buckle 226 and a tongue 227 are attached by a well-known method to the other end thereof. As shown in FIG. 19, a connection method of the band piece 221 and the housing 10 is a well-known method using a spring rod 225.

Returning to FIG. 18, another band piece 223 is connected to the lower end of the housing 10 at one end thereof. The connection method is similar to that shown in FIG. 19. Plural small holes 228 are formed in the band piece 223 at equal intervals along the longitudinal direction thereof. The band piece 223 is inserted into the buckle 226 and the tongue 227 is put through any one of the small holes 28, whereby the biometric measuring device is fixed to a human arm, and the back of the housing 10 is brought into tight contact with the back of the wrist. By selecting the small hole 28 through which the tongue 27 is passed, the perimeter of the device is adjusted. Details of the wristband 220 will be described hereinbelow.

FIG. 20 shows a cross section of the housing 10, and FIG. 21 is a perspective view showing the back side of the biometric measuring device. As will be understood from FIGS. 20 and 21, the housing 10 has the same structure as that of the housing 10 in the first embodiment shown in FIGS. 3 and 4. Therefore, a pulse wave as biometric information is detected by the same principle as that described above, and the pulse wave is analyzed and a pulse rate is displayed by the same method as that described above. To simplify the description, in the figures relating to the seventh embodiment, the components common to those of the first embodiment are indicated by the same reference numerals.

(2) Details of Wristband

The wristband 220 consists of the two band pieces 221 and 223, as described above. As shown in FIGS. 18, 20, and 21, the band piece 221 includes a base material 221a, and an elastic member 222 that is attached to the back of the base material 221a and is disposed inside when mounted to a living body. The band piece 223 also includes a base material 223a and an elastic member 224 that is attached to the back of the base material 223a and is disposed inside when mounted to the living body. The above-described buckle 226 and tongue 227 are attached to the base material 221a of the band piece 221, and the small holes 228 pass through the base material 223a of the band piece 223 and the elastic member 224. Therefore, the base materials 221a and 223a, and the housing 10 are wound all around a wrist W as shown in FIG. 22, and the device is attached to the wrist W. The elastic members 222 and 224 are disposed inside the base materials 221a and 223a, respectively, to be brought into tight contact with the wrist W.

By selecting the small hole 228 into which the tongue 227 is inserted, the position to interconnect the band pieces 221 and 223 by the tongue 227 and the buckle 226 can be varied. Therefore, the perimeter of the biometric measuring device can be changed according to the size of the wrist W.

The inside elastic members 222 and 224 are formed of a material having high flexibility and elasticity, while the outside base materials 221a and 223a are formed of a material having low flexibility and elasticity. For example, the elastic members 222 and 224 are formed of a material having high elasticity as compared with a base material, such as silicone, urethane foam rubber, or polyurethane rubber. In particular, polyurethane rubber may be preferable because it is inexpensive and can reduce the cost of manufacturing the device. On the other hand, the base materials 221a and 223a are formed of plastic having low elasticity, such as urethane, in a uniform density. As materials for these elastic members 222 and 224 and the base materials 221a and 223a, light-proof materials are selected in order to reduce measurement errors of the pulse wave sensor unit 100, which is an optical sensor.

The effect of the wristband 220 having elastic members 222 and 224 provided inside thereof in this way will be described with reference to FIGS. 22 and 11. FIG. 11 shows a biometric measuring device having the conventional wristband 30, which is formed of a single member and has circumferentially uniform flexibility. As described above, according to the conventional art, a gap may be formed between the LED 102 and the photodiode 103 of the pulse wave sensor unit 100, and the wrist, and external light may enter the gap. In addition, if wounding force is increased in order to prevent the entrance of the external light, the living body necessarily feels strong sensation of pressure and hence, it is difficult to use the device for a long time.

FIG. 22 shows a biometric measuring device having the wristband 220 of the above embodiment attached to the wrist of the test subject. According to this embodiment, since the elastic members 222 and 224 disposed inside have high elasticity, they easily expand and contract according to movement of the arm, and the housing 10 is difficult to separate from the wrist W. Therefore, the pulse wave sensor unit 10 resists the influence of the external light, and occurrence of the measurement errors can be reduced.

On the other hand, the force for holding the wrist W is secured by the base materials 221a and 223a having low elasticity. In other words, according to the band 220, holding ability against the wrist W can be secured by the base materials 221a and 223a having low elasticity and at the same time, movement, such as twisting of the wrist W, is permitted by the elastic members 222 and 224 disposed inside the base materials 221a and 223a. Therefore, it is possible to mount the device on a measurement site of the wrist W with high adhesion while minimizing the sensation of pressure, and measuring accuracy of the biometric measuring device is improved.

In addition, according to the wristband 220 of this embodiment, since a perimeter adjusting mechanism is formed by the buckle 226, the tongue 27, and the small holes 228, it is not necessary to prepare various types of bands even if the device is mounted to a site substantially varying in size among individuals, such as the human wrist, as compared with the conventional wristband 30 consisting of a single member. Therefore, it is possible to measure a number of test subjects using one device.

(3) Various Attaching Methods for Elastic Members

In the band pieces 221 and 223, methods for attaching the elastic members 222 and 224 to the base materials 221a and 223a include, for example, bonding with a bonding agent. However, it is preferable that the elastic members are detachably attached to the base materials according to the various methods described hereinbelow. It is considered that the elastic members may deteriorate or extend, and holding force against the living body may be weakened, and this concern grows as the device is repeatedly used. However, by making the elastic members attachable to and detachable from the base materials, the elastic members can be easily exchanged according to demand. In addition, although the elastic members contacting the living body are easily soiled, they can be easily exchanged even if they are soiled.

FIG. 23 shows a method for attaching the elastic member to the base material. According to the method, a number of penetrating small holes 40 are formed in a flat base material 221a, while a number of projections 41 are formed on the outer surface of a flat elastic member 222. As shown in a cross section enclosed with a circle A, the projection 41 is of mushroom shape which spreads at the pointed end thereof. When the base material 221a and the elastic member 222 are superposed, the projections 41 are fitted into the small holes 40, and once they are fitted, they do not easily fall out of the small holes 40 due to the spread pointed ends thereof. However, by applying a certain force, the base material 221a and the elastic member 222 can be separated from each other. Conversely, the small holes may be formed in the band piece, and the projections may be formed on the base material.

FIGS. 24 and 25 show another method for attaching the elastic member to the base material. According to this method, plural ribs 42 extending in the width direction are formed on the inner surface of an elastic member 222. Portions having no ribs 42 formed thereon are thin-walled portions 43. The outer surface of the elastic member 222 is flat, and is superposed on a flat base material 221a. The base material 221a and the elastic member 222 are pinched and fixed by U-shaped clips 44. More specifically, each of the clips 44 is slid in the width direction of a band piece 221 in such a manner that one side of each clip 44 comes into contact with the thin-walled portion 43, and the other side comes into contact with the outer surface of the base material 221a. The base material 221a and the elastic member 222 do not separate from each other by being pinched by the clips 44. However, by removing the clips 44 while sliding in the opposite direction, the base material 221a and the elastic member 222 can be separated from each other. Conversely, the ribs may be formed on the outer surface of the base material, or the ribs may not be provided.

FIGS. 26 and 27 show another method for attaching the elastic member to the base material. According to this method, although a flat auxiliary member 48 are disposed on the inside of a flat elastic member 222, the elastic member 222 partially projects toward the inner side than the auxiliary member 48. The auxiliary member 48 is formed of a material having low elasticity, such as urethane, similarly to the base material 221a, while the elastic member 222 is formed of silicone having the elasticity higher than that of the base material.

Plural projections 45 are formed on the inner surface of the elastic member 222, while plural penetrating holes 46 are formed in the auxiliary member 48. When the elastic member 222 and the auxiliary member 48 are superposed, the projections 45 are fitted into the holes 46 to project inward from the auxiliary member 48, as shown in a sectional view enclosed by a circle denoted by numeral A. Therefore, when mounting the biometric measuring device, the projections 45 of the elastic member 222 come into tight contact with the wrist W.

The elastic member 222 and the auxiliary member 48 superposed in this way are superposed on the flat base material 221a. The base material 221a, the elastic member 222, and the auxiliary member 48 are pinched and fixed by U-shaped clips 47. That is, each of the clips 47 is slid in the width direction of a band piece 221 in such a manner that one side of each clip 47 comes into contact with the inner surface of the auxiliary member 48, and the other side comes into contact with the outer surface of the base material 221a. The base material 221a, the elastic member 222, and the auxiliary member 48 do not separate from one another by being pinched by the clips 47. However, by removing the clips 47 while sliding in the opposite direction, they can be separated from one another.

According to the method shown in FIGS. 26 and 27, the projections 45 of the elastic member 222 partially come into tight contact with the wrist W. By contriving the layout of the projections 45, it is possible to increase the holding force against the wrist W, and reduce the sensation of pressure given to the wrist W, as compared with a case in which the elastic members come into tight contact with a wide area of the wrist W. The auxiliary member 48 is not necessarily required, and a biometric measuring device which is not provided therewith is included in the scope of the present invention. However, the provision of the auxiliary member 48 can protect the elastic member 222, which has high elasticity and deteriorate easily, from damage. For example, the damage of the elastic member 222 can be prevented from being damaged by the sliding of the clips 47.

Although FIGS. 23 to 27 show the construction of the band piece 221, the band piece 223 is constructed similarly. However, in order to jointly form small holes 228 of the band piece 223, through holes are formed in the base material 223 and the elastic member 224.

FIGS. 28 to 30B show another method for attaching the elastic member to the base material. According to this method, base materials 221a and 223a of band pieces 221 and 223 are inserted into elastic members 222a and 224a, respectively. As shown in FIG. 28, the base materials 221a and 223a of the band pieces 221 and 223 are flat, while the elastic members 222a and 224a include flat portions 50 and curved portions 51 integrally formed with the flat portions 50. Although the curved portions 51 are disposed on both ends of the flat portions 50 in this embodiment, the function thereof can be satisfied when at least one of the curved portions 51 is provided. The curved portions 51 and the flat portions 50 jointly form hollow sheaths 52.

As shown in FIGS. 29A and 29B, the base materials 221a and 223a are inserted into these sheaths 52. This allows the flat portions 50 of the elastic members 222a and 224a to be disposed inside of the base materials 221a and 223a so as to come into tight contact with the wrist W when attached to the wrist W. After being inserted in this way, the elastic members 222a and 224a do not separate from the base materials 221a and 223a due to their own elasticity. However, by applying a certain force, the elastic members 222a and 224a can be separated from the base materials 221a and 223a.

FIGS. 30A and 30B show the vicinity of a connected portion of the band pieces 221 and 223 in this biometric measuring device. In a state where the band pieces 221 and 223 are connected as shown in these figures, it is possible to insert a free end of the base material 223a of the band piece 223 into the sheath 52 of the elastic member 222a attached to the base material 221a of the band piece 221.

According to the band of this type in which a position to connect the band pieces 221 and 223 can be varied according to the size of the wrist W, since the free end of the band piece 223 projects, the free end may strike somewhere due to movement of the living body. For example, when the living body swings the wrist W, the free end may strike the body of the test subject. In such a case, the adhesion between the pulse wave sensor unit 100 and the wrist W is varied and the amount of light received is changed, whereby an accurate measurement cannot be carried out. According to this method, however, by inserting the free end of the base material 223a of the band piece 223 into the sheath 52 of the elastic member 222a, the movement of the free end is regulated and therefore, accuracy of the measurement can be maintained.

(4) Modification of Attaching Position of Elastic Member

While the elastic members 222 and 224 or the elastic members 222a and 224a come into contact with a wide area or a number of places of the wrist W in the seventh embodiment, a modification as shown in FIG. 31 can be made. According to this modification, an elastic member is provided only in the vicinity of a connected portion of the band pieces 221 and 223. More specifically, the elastic member 222 is disposed only in the vicinity of a buckle 226 and a tongue 227 in a base material 221a.

According to a band of this type in which the band pieces 221 and 223 are connected by the buckle 226, the tongue 227, and small holes 228, the buckle 226 and the tongue 227 may press the wrist W to provide an uncomfortable feeling. In particular, in the case of a thin test subject, since a tissue in the vicinity of a radial flexor tendon of wrist 60 is thin, the pointed end of the buckle 226 or the band piece 221 may press the tissue and test subject may feel a pain. However, the provision of an elastic member 222 in the vicinity of the buckle 226 and the tongue 227 can reduce or prevent the uncomfortable feeling. Any one of the methods for attaching the elastic member 222 to the base material 221a may be used.

(5) Display of Connecting Position

In the wristband 220, the band piece 223 having small holes 228 formed therein may preferably be provided with a display part which shows a connecting position, as shown in FIG. 32. According to the wristband 220, since the perimeter adjusting mechanism is formed by the buckle 226, the tongue 227, and the small holes 228, as described above, the perimeter of the biometric measuring device can be changed according to the size of the wrist W. However, in the case where the biometric measuring device is mounted to the same test subject, the band pieces 221 and 223 may preferably be connected to each other at the same position unless the perimeter of the device is changed, or unless the size of the wrist W is changed. Since the material having low flexibility is selected as a material for the base materials 221a and 223a in the wristband 220, the same small hole 228 may preferably be always used for the same test subject.

Thus, as shown in FIG. 32, numeral display part 70 may be provided on the outer surface of the base material 223a of the band piece 223. The numeral display part 70 has numerals disposed aside the small holes 228. These numerals are stamped or printed on the outer surface of the base material 223a, and become marks corresponding to plural of small holes 228.

In place of, or in addition to the numeral display part 70, a color display part may be provided. The color display part 71 has marks 72 disposed aside the small holes 228. The marks are printed or pasted on the outer surface of the base material 223a. The colors of the marks are different from one another, and are corresponding to plural small holes 228. The display of such connecting positions can be applied not only to the seventh embodiment, but also to all embodiments, as long as the perimeter adjusting mechanism is provided.

Eighth Embodiment

FIG. 33 shows a pulse-measuring device (biometric measuring device) 401 according to the eighth embodiment of the present invention. As shown in FIG. 33, the pulse-measuring device 401 consists of a wristwatch-type device main body 410, a cable 420 drawn out of the device main body 410, a finger-fitting unit 430 connected to an end of the cable 420, and a finger band 440 for fitting the finger-fitting unit 430 on a finger.

As shown in FIGS. 34 and 35, the finger-fitting unit 430 includes an inner casing 438, an outer casing 439, and a circuit board 436 whose both surfaces are fixed to the casings 438 and 439, respectively. An LED (light-emitting body) 431 and a photodiode (light-receiving body) 432 are mounted on the inner surface of the circuit board 436, and they are covered with the inner casing 438. On the other hand, an OP amplifier 434 and a circuit element 435 are mounted on the outer surface of the circuit board 436, and they are covered with the outer casing 439.

A transparent glass 437 is attached to the inner casing 438. The finger-fitting unit 430 is fitted on a finger so that the transparent glass 437 comes into tight contact with the surface of the finger of the test subject. When the LED 431 emits light, the light from the LED 431 passes through the transparent glass 437 to travel toward the finger, and reflected light from the finger passes through the transparent glass 437 to enter the photodiode 432. The photodiode produces an output signal according to the intensity of the entered light, and the OP amplifier 434 and the circuit element 435 amplify the output signal of the photodiode 432. The cable 420 is connected to the circuit board 436, and the amplified output signal is transmitted to the device main body 410 through the cable 420.

The finger band 440 is fixed to the outer casing 439. The finger band 440 can be wound all around the finger, and is fitted on the foot of the finger, as shown in FIG. 33. A lightproof material is selected for the material of the finger band 440. The finger band 440 may be in a flexible tubular form, or in a belt-like form. In the case of the belt-like form, an attaching tape known by a trade name "Velcro" may be attached to both ends of the finger band 440 so as to make the both ends detachable.

As described above, in the finger-fitting unit 430, the LED 431 and the photodiode 432 constitute a reflective optical sensor, and a pulse wave can be detected by the reflective optical sensor. That is, a part of the light illuminated from the LED 431 is absorbed by the tissue of the living body or hemoglobin in the blood, another part is reflected by the tissues of the living body, and the reflected light thereof is received by the photodiode 432. The photodiode 432 outputs an electric signal according to the amount of the light received. Therefore, the absorption by the tissues of the living body and the absorption by the hemoglobin in the blood are reflected in the output signal of the photodiode 432.

In the finger to which the LED 431 and the photodiode 432 are fitted, since blood in a capillary is influenced by the pulse wave, the absorbance may fluctuate with time. Therefore, fluctuations of the absorbance in the capillary in the finger are reflected in the output signal of the photodiode 432. That is, the output signal of the photodiode 432 fluctuates with the pulsation of the artery. Thus, the output signal of the OP amplifier 106 obtained by amplifying the output of the photodiode 432 can be regarded as a pulse wave signal. In this way, according to the eighth embodiment, the pulse wave is measured from bloodflow fluctuations in the capillary of the finger.

Returning to FIG. 33, the device main body 410 consists of a housing 10 containing therein a timepiece having the clocking function, and a wristband (living body pressure member) 20. On the front side of the housing 10, there is provided a liquid crystal device 413 for displaying pulse wave information (biometric information) and the like based on the detection results of the finger-fitting unit 430 in addition to the time and date. In addition, the housing 10 contains therein a data processing circuit 450 to which the pulse wave signal, which is the detection result of the finger-fitting unit 430, is supplied. The data processing circuit 450 treats the pulse wave for the fast Fourier transform processing (FFT processing), and analyzes the results to thereby calculate the pulse. Furthermore, button switches 411 and 412 for setting the time or switching display modes are provided on the outer surface of the housing 10.

The power source of the pulse-measuring device 401 is a non-illustrated buttery contained in the housing 10, and the cable 420 can supply electric power from the buttery to the finger-fitting unit 430 and input the detection results of the finger-fitting unit 430 into the data processing circuit 450 provided in the housing 10.

In the pulse-measuring device of this type, noise from body motions of the test subject may be included in the pulse wave signal. According to the analysis performed by the present inventors, it was found that the noise in the pulse wave signal obtained from a moving test subject included a number of components due to movement of the test subject such that a large acceleration was exerted on a measurement part of the test subject. For example, when the test subject bends an arm A with an elbow E as the fulcrum, as shown in FIG. 36A, the flow of blood is temporarily disturbed. However, at the moment when the test subject swings the forearm about the elbow E, the blood rapidly flows through arteries and arterioles toward the periphery of the arm due to centrifugal force. This influence reaches capillaries of a finger that is the object to be measured, and a noise component is generated in the pulse wave signal. Since blood-flow fluctuations due to bending and stretching of the arm A influences the pulse wave in this way, the pulse wave signal may be detected inaccurately. For the measurement of physical strength, the pulse-measuring device 401 is also used for measuring a pulse wave of the test subject during movement (such as running or walking). Therefore, it is preferable that the noise generated by the body motion of the test subject, such as bending and stretching of the arm A, be eliminated as much as possible.

As a technique capable of eliminating the noise generated by the body motion of the test subject, a portable pulse monitor having an acceleration sensor and an optical pulse sensor is known. According to the portable pulse monitor, a body motion signal detected by the acceleration sensor and a pulse wave signal detected by the optical pulse sensor are treated for the FFT processing so as to detect a body motion spectrum according to the body motion signal and a pulse wave spectrum according to the pulse wave signal, respectively. The pulse wave spectrum is compared with the body motion spectrum, a frequency component corresponding to the body motion spectrum is removed from the pulse wave spectrum, and a frequency of a spectrum having the maximum spectral intensity in the remaining spectrum is specified as a fundamental frequency of the pulse wave signal. Then, a pulse rate is calculated based on the fundamental frequency of the pulse wave signal. That is, in the conventional pulse monitor, the FFT processing is performed by two systems, and the pulse rate is calculated based on the results thereof.

However, since the above-described pulse monitor using the acceleration sensor must have two processing systems for performing the FFT processing, the construction becomes complicated and further, processing for specifying the fundamental frequency of the pulse wave signal from the frequency analysis results is required. In addition, when a living body moves violently, for example, when the living body swings an arm at high speed, the body motion spectrum is increased, it becomes difficult to relatively analyze the pulse wave spectrum, and it becomes difficult to calculate the pulse rate. In addition, when the living body moves in a disorderly way, a periodicity of the body motion signal detected by the acceleration sensor is eliminated, and it is difficult to compare the spectrums even if the FFT processing is performed.

Thus, in order to minimize the influence of the body motion with a simple construction, in this embodiment, the wristband 20 of the device main body 410 is brought into tight contact with the wrist of the test subject, and always presses arteries and arterioles in the wrist. For this purpose, the wristband 20 may be wound around the wrist with a strong holding force. However, if the force pressing on the wrist is increased, the test subject feels strong sensation of pressure, and it is therefore difficult to use the wristband for a long time. Therefore, according to this embodiment, the wristband 20 is used which is formed of a circumferentially flexible material, and in which the flexibility partially varies in the circumferential direction. In other words, the wristband 20 used in the eighth embodiment is the same as the wristband 20 of the first embodiment shown in FIGS. 1 to 4.

More specifically, as shown in FIG. 37, the wristband 20 has four band pieces 21 to 24. The short band piece 21 is connected to the upper end of the housing 10 at one end thereof, and is connected to one end of the long band piece 22 at the other end thereof. The connection method of the band piece 21 to the housing 10, and the connection method of the band pieces 21 and 22 are well-known ones using spring rods 25, as shown in FIG. 38, and they are mutually rotatable. In addition, the other short band piece 23 is connected to the lower end of the housing 10 at one end thereof, and is connected to one end of the long band piece 24 at the other end thereof. The connection method of the band piece 23 to the housing 10, and the connection method of the band pieces 23 and 24 are similar to the method shown in FIG. 38.

A buckle 26 and a tongue 27 are attached by a well-known method to an end of the band piece 22 that is farther away from the housing 10. In addition, although they are not shown in the figure, plural small holes are formed in the band piece 24 at equal intervals along the longitudinal direction thereof. The band piece 24 is inserted into the buckle 26, and the tongue 27 is put through any one of the small holes, whereby a device main body 410 is fixed to a wrist W of a test subject. By selecting the small hole through which the tongue 27 is inserted, the perimeter of the device main body 410 is adjusted. In this way, a perimeter adjusting mechanism is thus provided by the buckle 26, the tongue 27, and the small holes.

Of the band pieces 21 to 24 constituting the wristband 20, the short band pieces 21 and 23 near the housing 10 are formed of a material having high flexibility, while the long band pieces 22 and 24 far from the housing 10 are formed of a material having low flexibility. As a cross section is shown in FIG. 38, the band piece 21 consists of a central layer 21a, and fiber textile layers 21b secured to both sides thereof. The central layer 21a is formed of a material having high elasticity, such as urethane foam rubber or polyurethane rubber, and the fiber textile layer 21b is formed of textile that can follow expansion and contraction of the central layer 21a. Although it is not shown in the figure, the band piece 23 has a similar configuration. On the other hand, the band pieces 22 and 24 are formed of plastic having low elasticity, such as urethane, or of silicone, in a uniform density. The band pieces 21 to 24 in this embodiment may be either light-transmitting pieces or lightproof pieces.

The flexibility of the wristband 20 partially varies in the circumferential direction due to the difference in materials of the above band pieces 21 to 24. According to the wristband 20, movement, such as twisting of the wrist, is permitted by portions of the band having high flexibility (short band pieces 21 and 23), and holding ability against the wrist W can be secured by portions having low flexibility (long band pieces 22 and 24). That is, as shown by imaginary lines in FIG. 37, when the test subject twists the wrist W, the band pieces 22 and 24 follow the movement of the wrist W by expansion and contraction of the band pieces 21 and 23, and they remain in tight contact with the wrist W. Therefore, since the arteries and arterioles in the wrist W are always pressed, sudden bloodflow fluctuations in capillaries of a finger located on the downstream side (peripheral side) of the arteries and arterioles is controlled. The sensation of pressure given to the test subject can be minimized by the band pieces 21 and 23 having high flexibility.

The arteries and arterioles, which are nearer to the heart than the finger-fitting unit 430, are always pressed by the device main body 410 as described above, whereby a rapid bloodflow can be controlled (see FIGS. 36A and 36B) even if an external acceleration, in particular, an acceleration resulting from bending and stretching of the arm A during running or walking is exerted on the living body. This allows the bloodflow fluctuations during movement to be similar to those at rest. That is, it is possible to measure the pulse while minimizing the influence of body motions.

In order to partially vary the flexibility of the wristband 20 in the circumferential direction, it is possible to use the wristband 20 of the second to sixth embodiments shown in FIGS. 13 to 17 in place of the structure of the band shown in FIGS. 37 and 38. Even in these cases, the band pieces constituting the band may be either light-transmitting pieces or lightproof pieces.

In addition, in order to permit movement, such as twisting of the wrist W, and to secure holding ability against the wrist W, a wristband 220 of a modification described below may be used in place of the wristband 20. As shown in FIG. 39, the wristband 220 has two band pieces 221 and 223. The band piece 221 is connected to the upper end of a housing 10 at one end thereof, and a buckle 226 and a tongue 227 are attached by a well-known method to the other end thereof. The other band piece 223 is connected to the lower end of the housing 10 at one end thereof. The connection method of the band piece 221 to the housing 10, and the connection method of the band piece 223 to the housing 10 are similar to the well-known method shown in FIG. 38 using the spring rods 25.

Although they are not shown in the figure, plural small holes are formed in the band piece 223 at equal intervals along the longitudinal direction thereof. The band piece 223 is inserted into the buckle 226, and the tongue 227 is put through any one of the small holes, whereby a device main body 410 is fixed to a human arm. By selecting the small hole through which the tongue 227 is inserted, the perimeter of the device is adjusted. In this way, a perimeter adjusting mechanism is provided by the buckle 226, the tongue 227, and small holes.

The band piece 221 includes a base material 221a, and an elastic member 222 that is attached to the back of the base material 221a and is disposed inside when mounted on a living body. The band piece 223 also includes a base material 223a, and an elastic member 224 that is attached to the back of the base material 223a and is disposed inside when mounted on a living body. The above-described buckle 226 and the tongue 227 are attached to the base material 221a of the band piece 221, and the small holes pass through the base material 223a of the band, piece 223 and the elastic members 224. Therefore, the base materials 221a and 223a, and the housing 10, are wound all around a wrist W, as shown in FIG. 39, and the device main body 410 is attached to the wrist W. The elastic members 222 and 224 are disposed inside the base materials 221a and 223a, respectively, to be brought into tight contact with the wrist W.

The inside elastic members 222 and 224 are formed of a material having high flexibility and elasticity, while the outside base materials 221a and 223a are formed of a material having low flexibility and elasticity. For example, the elastic members 222 and 224 are formed of a material having high elasticity as compared with a base material, such as silicone, urethane foam rubber, or polyurethane rubber. On the other hand, the base materials 221a and 223a are formed of plastic having low elasticity, such as urethane, in a uniform density. That is, the wristband 220 in the modification shown in FIG. 39 is equivalent to the wristband 220 of the seventh embodiment shown in FIGS. 18 to 22.

In the band pieces 221 and 223, methods for attaching the elastic members 222 and 224 to the base materials 221a and 223a include, for example, bonding with a bonding agent. However, it is possible to apply the above-described various methods shown in FIGS. 23 to 30B. It is preferable that the elastic members be detachably attached to the base materials according to these methods. This allows the elastic members to be easily exchanged when the material of the elastic members deteriorates or the material is soiled in appearance.

According to the wristband 220 having the elastic members 222 and 224 thus provided on the inside thereof, movement, such as twisting of the wrist W, is permitted by the elastic members 222 and 224, and holding ability against the wrist W can be secured by portions having low elasticity (base materials 221a and 223a). That is, as shown by imaginary lines in FIG. 39, when the test subject twists the wrist W, the elastic members 222 and 224 follow the movement of the wrist W by expansion and contraction of the elastic members 222 and 224, and they remain in tight contact with the wrist W. Therefore, since arteries and arterioles in the wrist W are always pressed, sudden bloodflow fluctuations in capillaries in a finger located on the downstream side (peripheral side) of the arteries and arterioles is controlled. The sensation of pressure given to the test subject can be minimized by the elastic members 222 and 224.

The arteries and arterioles, which are nearer to the heart than the finger-fitting unit 430, are always pressed by the device main body 410 as described above, whereby a rapid bloodflow can be controlled (see FIGS. 36A and 36B) even if an external acceleration, in particular, an acceleration resulting from bending and stretching of the arm A during running or walking is exerted on the living body. This allows the bloodflow fluctuations during movement to approach those at rest. That is, it is possible to measure the pulse while minimizing the influence of the body motion.

An experiment relating to this superior effect will be described below. According to the experiment, a device main body 410 was prepared in which elastic members 222 and 224 were attached to base materials 221a and 223a according to the method shown in FIG. 23. For comparison, a device main body 110 was prepared which had a conventional wristband 131 made of a single urethane member and in which circumferential flexibility was not considered. Pulse-measuring devices having the device main body 410 and 130, respectively, were attached on plural test subjects, and the test subjects ran on a treadmill (running machine). The device main body 410 according to this embodiment was attached so that the test subject felt a slight sensation of pressure, while the device main body 130 for comparison was attached to produce a sensation such as the test subject would generally feel when attaching a watch thereon.

In both cases, a pulse wave signal detected by the finger-fitting unit 430 was treated for the FFT processing to obtain a pulse wave spectrum. In addition, an acceleration sensor was fitted on a finger, a body motion signal detected by the acceleration sensor was treated for the FFT processing to obtain a body motion spectrum (noise spectrum).

FIG. 41 shows the experimental results. In the figure, a line "a" represents a measurement result (average of plural test subjects) relating to the device main body 410 according to this embodiment, and a line "b" represents a measurement result relating to the device main body 130 for comparison. In addition, in the figure, the horizontal axis shows the running speed of the test subject, that is, the vigor of movement. The running speed can be varied on the treadmill. The vertical axis shows the ratio of the intensity of a fundamental wave in the pulse wave spectrum to the intensity of a fundamental wave in the noise spectrum. The higher the ratio, the better SN ratio of the pulse wave signal can be obtained. As is apparent from FIG. 41, in all movement load areas, it was confirmed that the pulse-measuring device according to this embodiment had a better SN ratio.

In particular, when the running speed was higher than 8 km/h, according to the comparative sample, the ratio of the pulse wave to the noise was less than 1, that is, the intensity of the pulse wave spectrum was lower than the intensity of the noise spectrum. In contrast, according to the pulse-measuring device of this embodiment, the ratio of the pulse wave to the noise was larger than 1 even if the running speed was higher than 8 km/h (that is, the intensity of the pulse wave spectrum was higher than the intensity of the noise spectrum). In other words, if the arm was swung violently as in running, the intensity of the pulse wave spectrum was higher than the intensity of the noise spectrum. Therefore, when the pulse wave signal is treated for the FFT processing as in this embodiment, the frequency having the highest spectrum can be regarded as a pulse rate. This can measure the pulse accurately without detecting the body motion spectrum for comparison. Therefore, since two processing systems for performing the FFT processing are not required, the construction of the device is simplified.

While the pulse wave signal is treated for the FFT processing by the data processing circuit 450 in the housing 10, and the pulse rate is calculated by analyzing the processing results in the above-described embodiment, the pulse wave signal may be converted into a rectangular wave signal, and the pulse rate may be calculated based on the cycle of the rectangular wave signal. Even if the arm is swung as in daily life, the pulse can be measured accurately.

Ninth Embodiment

The ninth embodiment according to the present invention will now be described. As shown in FIG. 42, a pulse-measuring device (biometric measuring device) 301 of the ninth embodiment is of a unitized wristwatch type, and includes a housing (support body) 10 storing therein various electrical or electronic parts, and a wristband 320 connected to the housing 10 and wound around a human arm to fix the housing 10 to the arm.

The wristband 320 of this embodiment has two band pieces 321 and 323. The band piece 321 is connected to the upper end of the housing 10 at one end thereof, and a buckle 326 and a tongue 327 are attached by a well-known form to the other end thereof. As shown in FIG. 43, the connection method of the band piece 321 to the housing 10 is a well-known method using spring rods 325.

Returning to FIG. 42, the other band piece 323 is connected to the lower end of the housing 10 at one end thereof. The connection method is similar to that shown in FIG. 43. Plural small holes 328 are formed in the band piece 323 at equal intervals along the longitudinal direction thereof The band piece 323 is inserted into the buckle 326 and the tongue 327 is put through any one of the small holes 328, whereby the pulse-measuring device 301 is fixed to a human arm, and the back of the housing 10 is brought into tight contact with the back of the wrist. By selecting the small hole 328 through which the tongue 327 is inserted, the perimeter of the pulse-measuring device 301 is adjusted. Details of the wristband 320 will be described hereinbelow.

As a cross section is shown in FIG. 43, the housing 10 is equivalent to the housing 10 used in the first embodiment shown in FIG. 3, and has an LED 102 which is a light-emitting body, and a photodiode 103 which is a light-receiving body. Light emitted from the LED 102 travels downward in the figure to illuminate the wrist of a person who has the device mounted thereon. The illumination light is absorbed by tissues or blood vessels of the wrist, and the illumination light which is not absorbed is reflected. The reflected light is received by the photodiode 103, and the photodiode 103 generates an electric signal corresponding to the intensity of the light received. To simplify the description, the components common to those of the first embodiment in the figures relating to the ninth embodiment are indicated by the same reference numerals as those of the figures of the first embodiment.

A back cover 12 has a bent shape as shown in the figure, whereby a protuberance 12a protruding toward the back side is formed. The central part of the protuberance 12a is flat, and a transparent glass 104 for protecting the LED 102 and the photodiode 103 and permitting transmission of light is provided on the central portion of the protuberance 12a.

By the same principle as that described about the first embodiment, an output signal of an OP amplifier 106 obtained by amplifying the output of the photodiode 103 can be regarded as a pulse wave signal. According to this embodiment, a pulse wave is measured from bloodflow fluctuations in arteries and arterioles of the wrist (particularly, the arterioles near the back of the wrist). By the same method as that of the first embodiment, the pulse is calculated, and is displayed on a liquid crystal display device 113.

The wristband 320 for winding the pulse-measuring device 301 around a wrist of a test subject consists of two band pieces 321 and 323 as described above. A single elastic member (living body-pressing member) 330 is attached to the band pieces 321 and 323, and a great part of the elastic member 330 is disposed on the back side of the band pieces 321 and 323, that is, on the inside when the housing 10 is attached to the wrist.

The inside elastic member 330 is formed of a material having high flexibility and elasticity, while the outside band pieces 321 and 323 are formed of a material having low flexibility and elasticity. For example, the elastic member 330 is formed of a material having high elasticity as compared with the band pieces 321 and 323, such as silicone, urethane foam rubber, or polyurethane rubber. In particular, polyurethane rubber may be preferable because it is inexpensive and can reduce the cost of manufacturing the device. On the other hand, the band pieces 321 and 323 are formed of plastic having low elasticity, such as urethane, in a uniform density. As materials for these elastic member 330 and the band pieces 321 and 323, lightproof materials are selected in order to reduce measurement errors of a pulse wave sensor unit 100, which is an optical sensor.

As shown in FIG. 44, the elastic member 330 includes a ring-shaped central portion 331, and tongue portions 332 and 333 extending at both sides thereof, and the central portion 331 and the tongue portions 332 and 333 are evenly formed on the same plane. A through hole 331a is formed in the central portion 331. Curved portions 334 are integrally formed with the tongue portions 332 and 333, respectively. Although two curved portions 334 are formed on the tongue portions 332 and 333, respectively, in this embodiment, the function thereof can be satisfied when at least one of the curved portions 334 is provided. The curved portions 334 and the tongue portions 332 and 333 jointly form hollow sheaths 335.

As shown in FIGS. 45A and 45B, the band pieces 321 and 323 are inserted into the sheaths 335. This allows the central portion 331 of the elastic member 330 and the tongue portions 332 and 333 to be disposed inside the band pieces 321 and 323 so as to come into tight contact with the wrist W when attached to the wrist W. After being inserted in this way, the elastic member 330 does not separate from the band pieces 321 and 323 due to their own elasticity. However, by applying a certain force, the elastic member 330 can be separated from the band pieces 321 and 323. By making the elastic member 330 attachable to and detachable from the band pieces 321 and 323, which are the base materials, the elastic member 330 can be easily exchanged according to demand. In addition, although the elastic member 330 contacting a living body is easily soiled, it can be easily exchanged even if it is soiled.

In addition, as shown in FIG. 45B, the protuberance 12a of the above-described housing 10 is fitted into the through hole 331a of the central portion 331 of the elastic member 330. Therefore, the transparent glass 104 provided on the protuberance 12a comes into tight contact with the wrist W when the pulse-measuring device 301 is attached to the wrist W.

In this way, according to the wristband 320 having the elastic member 330 provided inside thereof, since the elastic member 330 disposed inside has high elasticity, it easily expands and contracts according to movement of the arm, and the transparent glass 104 provided on the housing 10 is difficult to separate from the wrist W. Therefore, the pulse wave sensor unit 100 resists the influence of external light, and occurrence of measurement errors can be reduced.

On the other hand, the force for holding the wrist W is secured by the band pieces 321 and 323 having low elasticity. In other words, holding ability against the wrist W can be secured by the band pieces 321 and 323 having low elasticity and at the same time, movement, such as twisting of the wrist W, is permitted by the elastic member 330 disposed inside the band pieces 321 and 323. Therefore, it is possible to mount the device on a measurement site of the wrist W with high adhesion while minimizing the sensation of pressure, and measuring accuracy of the biometric measuring device is improved.

In addition, as shown in FIG. 42, in a state where the band pieces 321 and 323 are connected, it is possible to insert a free end 323a of the band piece 323 into the sheath 335 attached to the band piece 321. According to the band of this type in which a position to connect the band pieces 321 and 323 to each other can be varied according to the size of the wrist W, since the free end 323a of the band piece 323 projects, the free end may strike somewhere due to movement of the living body. For example, when the living body swings the wrist W, the free end 323a may strike the body of the test subject. In such a case, the adhesion between the pulse wave sensor unit 100 and the wrist W is fluctuated and the amount of light received is changed, whereby an accurate measurement cannot be carried out. According to this method, however, by inserting the free end 323a of the band piece 323 into the sheath 335 of the elastic member 330, the movement of the free end 323a is regulated and therefore, accuracy of the measurement can be maintained.

Further, as described above, the protuberance 12a of the above housing 10 is fitted into the through hole 331a of the central portion 331 of the elastic member 330 (see FIG. 45B). Therefore, in the pulse wave sensor unit 100, the elastic member 330 always exists on the side nearer to the heart than the transparent glass 104 through which light passes, and arteries and arterioles, which are nearer to the heart, are always pressed by the elastic member 330. Therefore, sudden bloodflow fluctuations is controlled on the downstream side thereof. The sensation of pressure given to the test subject can be minimized by the elastic member 330.

The arteries and arterioles, which are nearer to the heart than the transparent glass 104, are always pressed by the elastic member 330 as described above, whereby a rapid bloodflow can be controlled (see FIGS. 36A and 36B) even if an external acceleration, in particular, an acceleration resulting from bending and stretching of the arm A during running or walking is exerted on the living body. This allows the bloodflow fluctuations during movement to approach those at rest. That is, it is possible to measure the pulse while minimizing the influence of the body motion.

An experiment relating to this superior effect will be described below. According to the experiment, a pulse-measuring device 301 according to this embodiment was prepared. For comparison, a pulse wave-measuring device 301 was prepared which does not use the elastic member 330. Pulse-measuring devices having the device main body 410 and 130, respectively, were attached on plural test subjects, and the test subjects ran on a treadmill. The pulse-measuring device 301 according to this embodiment was attached so that the test subject felt a slight sensation of pressure, while the device main body 130 for comparison was attached to produce a sensation such as the test subject would generally feel when attaching a watch thereon.

In both cases, the detected pulse wave was treated for the FFT processing to obtain a pulse wave spectrum. In addition, an acceleration sensor was fitted on a finger, a body motion signal detected by the acceleration sensor was treated for the FFT processing to obtain a body motion spectrum (noise spectrum).

FIG. 46 shows the experimental results. In the figure, a line "c" represents a measurement result (average of plural test subjects) relating to the pulse-measuring device 301 according to this embodiment, and a line "d" represents a measurement result relating to the device for comparison. In addition, in the figure, the horizontal axis and the vertical axis are similar to those shown in FIG. 41. As is apparent from FIG. 46, in all movement load areas, it was confirmed that the pulse-measuring device according to this embodiment had a better SN ratio.

In particular, when the running speed was higher than 8 km/h, according to the comparative sample, the ratio of the pulse wave to the noise was less than 1, that is, the intensity of the pulse wave spectrum was lower than the intensity of the noise spectrum. In contrast, according to the pulse-measuring device of this embodiment, the ratio of the pulse wave to the noise was larger than 1 even if the running speed was higher than 8 km/h (that is, the intensity of the pulse wave spectrum was higher than the intensity of the noise spectrum). In other words, if the arm was swung violently as in running, the intensity of the pulse wave spectrum was higher than the intensity of the noise spectrum. Therefore, when the pulse wave signal is treated for the FFT processing as in this embodiment, the frequency having the highest spectrum can be regarded as a pulse rate. This can measure the pulse accurately without detecting the body motion spectrum for comparison. Therefore, since two processing systems for performing the FFT processing are not required, the construction of the device is simplified.

In order to always press the portion that is nearer to the heart than the transparent glass 104, an elastic member 330A of a modification shown in FIGS. 47A and 47B may be used. The elastic member 330A has a circular arc-shaped central portion 331A instead of the ring-shaped central portion 331 (see FIG. 44), but the other features are similar to those of the above-described elastic member 330. The protuberance 12a of the above housing 10 is fitted into a recess 331Aa of the central portion 331A. When the pulse-measuring device 301 of this modification is attached to the wrist W, the central portion 331A is located nearer to the heart than the transparent glass 104.

Tenth Embodiment

The tenth embodiment according to the present invention will now be described. As shown in FIG. 48, a pulse-measuring device (biometric measuring device) 301 is of a unitized wristwatch type, has the same basic configuration as that of the ninth embodiment, and the principle of measurement of pulse is also same as that of the ninth embodiment. Therefore, in FIG. 48, components common to those of the ninth embodiment are indicated by the same reference numerals, and a description thereof will be omitted.

In the pulse-measuring device 301 according to the tenth embodiment;, separate elastic members 340 are attached to band pieces 321 and 323, respectively. A material of the elastic members 340 is similar to that of the above elastic member 330. The elastic members 340 include flat portions 341 and curved portions 342 integrally formed with the flat portions 341. According to this embodiment, although the curved portions 342 are disposed on both ends of the flat portions 341, the function thereof can be satisfied when at least one curved portion 342 is provided. The curved portions 342 and the flat portions 341 jointly form hollow sheaths 345.

The band pieces 321 and 323 are inserted into the sheaths 345. This allows the flat portions 341 of the elastic members 340 to be disposed inside the band pieces 321 and 323 so as to come into tight contact with a wrist W when attached to the wrist W. After being inserted in this way, the elastic members 340 do not separate from the band pieces 321 and 323 due to their own elasticity. However, by applying a certain force, the elastic members 340 can be separated from the band pieces 321 and 323. Although it is not shown in the figure, in a state where the band pieces 321 and 323 are connected, it is possible to insert a free end of the band piece 323 into the sheaths 345 of the elastic member 340 attached to the band piece 321.

The elastic members, however, are not limited to the elastic members 340 shown in FIGS. 48A and 48B, and the elastic members 222 and 224 shown in FIG. 39, or elastic members of the attaching methods shown in FIGS. 23 to 27 may be used. Since the thus-disposed inside elastic members disposed inside in this way have high flexibility, they easily contract following movement of the arm, and a transparent glass 104 provided on a housing 10 is difficult to separate from the wrist W. Therefore, the pulse wave sensor unit 100 resists the influence of external light, and occurrence of measurement errors can be reduced. On the other hand, the force for holding the wrist W can be secured by the band pieces 321 and 323 having low elasticity.

In addition, according to this embodiment, a protuberance 12a of a back cover 12 of the housing 10 is formed in asymmetrical with respect to the center line C of a wristband 320, as shown in FIG. 48B. On the other hand, the transparent glass 104 provided on the housing 104 is symmetric with respect to the center line C. Therefore, in the protuberance 12a, a wide flat portion (living body-pressing member) 370 is located nearer one side than the transparent glass 104. When the pulse-measuring device 301 is attached to the wrist, not only the transparent glass 104, but also the flat portion 370 comes into tight contact with the wrist. In addition, when the pulse-measuring device 301 is attached to the wrist, the flat portion 370 is located nearer to the heart than the transparent glass 104, and always presses arteries and arterioles near the heart. This allows a rapid bloodflow to be controlled even if an external acceleration, in particular, an acceleration resulting from bending and stretching of an arm A during running or walking is exerted on the living body. Therefore, the bloodflow fluctuations during movement can be approached those at rest. That is, it is possible to measure the pulse while minimizing the influence of the body motion.

Modifications

In the above-described embodiments, the perimeter adjusting mechanism is provided by the buckle 26, 226, or 326, the tongue 27, 227, or 327, and the small holes 28, 228, or 328. However, the perimeter adjusting mechanism is not limited thereto, and an attaching tape known by a trade name "Velcro" possessed by Velcro Industries B.V., a button, and the like may be used. In addition, in the above embodiments except the modifications shown in FIGS. 31 and 32, the perimeter adjusting mechanism is not necessarily required, and a modification which is not provided with the perimeter adjusting mechanism falls within the scope of the present invention.

While the foregoing description of embodiments and modifications enable those skilled in the art to practice the present invention, the present invention is not intended to be limited to the above-described embodiments and modifications, and any modifications and amendments fall within the scope of the present, invention as long as they are based on the principle disclosed herein.

What is claimed is:

1. A biometric measuring device, comprising:

a light-emitting means for applying light to a detection site on a living body;

a biometric information detection means for receiving reflected light from said living b9dy of the light applied by said light-emitting means to produce a biometric information signal according to the reflected light received;

a support body for supporting said light-emitting means and said biometric information detection means;

a band connected to said support body to be wound around said living body near said detection site to fix said support body to said living body;

wherein said band includes an outer support strap fixed to said support body and a resiliently compressible insert attached to an outer surface of said strap so that said insert is in contact with, and between, said living body and said strap when said band is wound around said living body, said insert being detachable from said strap without requiring removal of said strap from said support body; and a living body pressing means adapted to be disposed on a portion closer to a heart of the living body than said biometric information detection means and adapted to adhere to the living body to press the living body, said pressing means being effective for applying a restraining pressure to said living body sufficient for mitigating blood flow fluctuations within said detection site irrespective of movement of said detection site by said living body during a period of dynamic activity by said living body.

2. A biometric measuring device, comprising:

a light-emitting body for applying light to a detection site on a living body;

a light-receiving body for receiving reflected light from said living body of the light applied by said light-emitting body to produce a biometric information signal according to the reflected light received;

a support body for supporting said light-emitting body and said light-receiving body;

a band connected to said support body to be wound around said living body near said detection site to fix said support body to said living body;

wherein said band includes an outer support strap fixed to said support body and a resiliently compressible insert attached to an outer surface of said strap so that said insert is in contact with, and between, said living body and said strap when said band is wound around said living body, said insert being detachable from said strap without requiring removal of said strap from said support body; and a living body pressing member adapted to be disposed on a portion closer to a heart of the living body than said light-receiving body and adapted to adhere to the living body to press the living body, said pressing member being effective for applying a restraining pressure to said living body sufficient for mitigating blood flow fluctuations within said detection site irrespective of movement of said detection site by said living body during a period of dynamic activity by said living body.

3. A device according to claim 1 or 2, wherein said insert is effective for maintaining said support body in substantially uniform surface contact with said living body irrespective of movement by said living body.

4. A device according to claim 1 or 2, wherein said strap includes one of a plurality of holes and a plurality of projections, and wherein said insert includes the other one of said plurality of holes and said plurality of projections for mating with, and attaching to, said strap.

5. A device according to claim 1 or 2, wherein said band further includes at least one clip for securing said insert to said strap.

6. A device according to claim 1 or 2, wherein said strap is not stretchable.

7. A device according to claim 1 or 2, wherein said insert is made of polyurethane rubber.

8. A device according to claim 1 or 2, wherein said insert includes at least one retaining loop into which said strap is inserted for securing said insert to said strap.

9. A device according to claim 1, wherein said strap is fixed to opposing sides of said support body and said insert spans under said support body across said opposing sides, said support body having a protrusion on its underside alongside part of said insert, said protrusion making contact with said living body when said band is wound around said living body.

10. A device according to claim 9:

wherein said insert has a through hole positioned under said support body; and wherein said protrusion houses said light-emitting means and said biometric information detection means and is inserted in said through hole.

11. A device according to Claim 2, wherein said strap is fixed to opposing sides of said support body and said insert spans under said support body across said opposing sides, said support body having a protrusion on its underside alongside part of said insert, said protrusion making contact with said living body when said band is wound around said living body.

12. A device according to claim 11:

wherein said insert has a through hole positioned under said support body; and wherein said protrusion houses said light-emitting body and said light-receiving body and is inserted in said through hole.

13. A biometric measuring device, comprising:

a light-emitting means for applying light to a detection site on a living body;

a biometric information detection means for receiving reflected light from said living body of the light applied by said light-emitting means to produce a biometric information signal according to the reflected light received;

a support body for supporting said light-emitting means and said biometric information detection means; and a band connected to said support body to be wound around said living body near said detection site to fix said support body to said living body;

wherein said band comprises a base material to be wound around the living body and an elastic member attached to an outer surface of said base material so that said elastic member is in contact with, and between, said living body and said base material when said band is wound around said living body, said elastic member having a flexibility higher than that of said base material, said elastic member being detachable from said base material, said base material being not stretchable.

14. A biometric measuring device, comprising:

a light-emitting body for applying light to a detection site on a living body;

a light-receiving body for receiving reflected light from said living body of the light applied by said light-emitting body to produce a biometric information signal according to the reflected light received;

a support body for supporting said light-emitting body and said light-receiving body; and a band connected to said support body to be wound around said living body near said detection site to fix said support body to said living body;

wherein said band has a base material to be wound around the living body and an elastic member attached to an outer surface of said base material so that said elastic member is in contact with, and between, said living body and said base material when said band is wound around said living body, said elastic member having a flexibility higher than that of said base material, said elastic member being detachably attached to said base material, said base material being not stretchable.

15. A device according to claim 13 or 14, wherein said elastic member is effective for maintaining said support body in substantially uniform surface contact with said living body irrespective of movement by said living body.

16. A device according to claim 13 or 14, wherein said base material comprises one of plural holes and plural projections wherein said elastic member comprises the other one of said plural holes and said plural projections.

17. A device according to claim 16, wherein when said projections are inserted into said holes, said projections are secured to said holes whereby said elastic member is detachably attached to said base material.

18. A device according to claim 13 or 14, further comprising a clip to secure said base material to said elastic member.

19. A device according to claim 18, wherein said elastic member comprises a groove in which said clip is located.

20. A device according to claim 13 or 14, wherein said elastic member includes a retaining loop into which said base material is inserted.

21. A device according to claim 13 or 14, wherein said band includes plural band pieces, and a connecting member for mutually connecting said plural band pieces, a position to connect said plural band pieces with said connecting member according to the size of the living body which is variable, at least one of said plural band pieces comprises a second elastic member, and said second elastic member controls movement of another one of said plural band pieces.

22. A device according to any one of claims 1, 2, 6 and 14, wherein said band includes plural band pieces, and a connecting member for connecting said plural band pieces to each other, a position to connect said plural band pieces with said connecting member according to a size of the living body which is variable, and a display part for displaying a position to connect said plural band pieces by said connecting member is provided on an outer surface of said band.

23. A biometric measuring device comprising:
a light-emitting means for applying light to a detection site on a living body;
a biometric information detection means for receiving reflected light from said living body of the light applied by said light-emitting means to produce a biometric information signal according to the reflected light received;
a support body for supporting said light-emitting means and said biometric information detection means;
a band connected to said support body to be wound around said living body near said detection site to fix said support body to said living body; and
a living body pressing means adapted to be disposed on a portion closer to a heart of the living body than said biometric information detection means adapted to adhere and adhering to the living body to press the living body, said pressing means being effective for applying a restraining pressure to said living body sufficient for mitigating blood flow fluctuations within said detection site irrespective of movement of said detection site by said living body during a period of dynamic activity by said living body.

24. A device according to claim 13, wherein said living body pressing means is constituted by said band.

25. A biometric measuring device comprising:
a light-emitting body for applying light to a detection site on a living body;
a light-receiving body for receiving reflected light from said living body of the light applied by said, light-emitting body to produce a biometric information signal according to the reflected light received;
a support body for supporting said light-emitting body and said light-receiving body;
a band connected to said support body to be wound around said living body near said detection site to fix said support body to said living body; and
a living body pressing member adapted to be disposed on a portion closer to a heart of the living body than said light-receiving body and adapted to adhere to the living body to press the living body, said pressing member being effective for applying a restraining pressure to said living body sufficient for mitigating blood flow fluctuations within said detection site irrespective of movement of said detection site by said living body during a period of dynamic actvity by said living body.

26. A device according to claim 25, wherein said band has a base material to be wound around the living body; and an elastic member attached to an outer surface of said base material so that said elastic member is in contact with, and between, said living body and said base material when said band is wound around said living body, said elastic member having a flexibility higher than that of said base material, said elastic member being detachably attached to said base material; and
said living body pressing member being constituted by said elastic member of said band.

27. A device according to claim 25, wherein said living body pressing member is constituted by said band.

28. A device according to claim 25, wherein said support body comprises a protuberance, and said band comprises a portion into which said protuberance is fitted.

29. A biometric measuring device for use during dynamic activity by a user having a living body, comprising:
a light-emitting means for applying light to a target area on the living body of said user;
a light-receiving means for receiving reflected light from said living body of the light applied by said light-emitting means to produce a biometric information signal according to the reflected light received; and
a living body pressing member adapted to be disposed on a portion closer to a heart of said living body than said light-receiving means, and adapted to adhere to said living body to press said living body sufficiently for mitigating fluctuations in blood flow within said target area irrespective of movement of said target area by said living body;
wherein said body pressing member includes a display module attached to a band to be wound around said living body, said band having an outer support strap fixed to said display module and a resiliently compressible insert attached to an outer surface of said strap so that said insert is in contact with, and between, said living body and said strap when said band is wound around said living body, said insert being effective for maintaining pressure contact with interior blood vessels of said living body irrespective of twisting motion by said living body.

30. A biometric measuring device for use during dynamic activity by a user, comprising:
a light-emitting body for applying light to a target area of the living body of said user;
a light-receiving body for receiving reflected light from said living body of the light applied by said light-emitting body to produce a biometric information signal according to the reflected light received; and
a living body pressing member adapted to be disposed on a portion closer to a heart of said living body than said light-receiving body and adapted to adhere to said living body to press said living body sufficiently for mitigating fluctuations in blood flow within said target area irrespective of movement of said target area by said living body;
wherein said body pressing member includes a data processing module attached to a band to be wound around said living body, said band having an outer support strap fixed to said data processing module and a resiliently compressible insert attached to an outer surface of said strap so that said insert is in contact with, and between, said living body and said strap when said band is wound around said living body, said insert being effective for maintaining pressure contact with interior blood vessels of said living body irrespective of twisting motion by said living body.

31. A biometric measuring device according to claim 30, wherein:

said display module receives as an input said biometric information signal produced by said light-receiving body and processes said biometric information signal; and wherein said light-emitting body and said light-receiving body are attached to a finger-fitting body adapted to be fitted on a finger of said living body.

32. A biometric measuring device according to claim 31, wherein said band comprises a circumferentially flexible material and flexibility thereof partially varies in a circumferential direction.

33. A biometric measuring device according to claim 31, wherein said band comprises a base material to be wound around the living body and an elastic member disposed inside of said base material and having a flexibility higher than that of said base material.

34. A device according to claim 33, wherein said living body pressing member is constituted by said elastic member of said band.

35. A biometric measuring device according to claim 30, wherein:

said data processing module further functions to support said light-emitting body and said light-receiving body.

* * * * *

UNITED STATES PATENT AND TRADEMARK OFFICE
CERTIFICATE OF CORRECTION

PATENT NO.    : 6,529,754 B2
DATED         : March 4, 2003
INVENTOR(S)   : Yutaka Kondo It is certified that error appears in the above-identified patent and that said Letters Patent is hereby corrected as shown below:

Column 26,
Line 45, change "b9dy" to -- body --.

Column 29,
Line 52, change "Claim 13" to -- Claim 23 --.

Signed and Sealed this

Ninth Day of September, 2003

JAMES E. ROGAN
*Director of the United States Patent and Trademark Office*